United States Patent [19]

Ahlquist et al.

[11] 3,953,127
[45] Apr. 27, 1976

[54] PHOTON-COUNTING INTEGRATING NEPHELOMETER

[75] Inventors: Norman C. Ahlquist; Alan P. Waggoner; Robert J. Charlson, all of Seattle, Wash.

[73] Assignee: Battelle Development Corporation, Columbus, Ohio

[22] Filed: Aug. 16, 1974

[21] Appl. No.: 498,278

Related U.S. Application Data

[63] Continuation-in-part of Ser. No. 435,734, Jan. 23, 1974, abandoned, which is a continuation of Ser. No. 351,609, April 16, 1973, abandoned.

[52] U.S. Cl. .............................. 356/103; 250/574
[51] Int. Cl.² ........................................ G01N 21/00
[58] Field of Search ............. 356/103, 104, 102, 39, 356/226; 250/207, 574

[56] References Cited
UNITED STATES PATENTS

| | | | |
|---|---|---|---|
| 3,563,661 | 2/1971 | Charlson et al. | 356/103 |
| 3,671,128 | 6/1972 | Radke et al. | 356/103 |

OTHER PUBLICATIONS

Birenbaum, L., et al., "Photomultiplier Single Photon Counting Efficiency", Applied Optics, Vol. 12, No. 3, (519).

*Primary Examiner*—John K. Corbin
*Assistant Examiner*—Conrad Clark
*Attorney, Agent, or Firm*—Christensen, O'Connor, Garrison & Havelka

[57] ABSTRACT

An improved integrating nephelometer having superior sensitivity and long-term stability to previous designs includes a container defining a measurement chamber. A continuously energized light source, such as a tungsten filament incandescent bulb, illuminates the measurement chamber through an opal glass diffuser. The intensity of the light source is regulated in one embodiment by a simple optical-electric feedback system, and in another embodiment by a voltage regulated supply. A cone of observation of the chamber is defined by a plurality of spaced, apertured plates located in the chamber, at right angles to the light source. A measuring photomultiplier tube views the cone of observation and provides an output signal including components resulting from detected photoelectrons, noise, and thermally emitted "dark current" electrons. A photon-detecting apparatus removes the noise component and provides an output pulse for each photoelectron and "dark current" electron. The output pulses are counted, and converted into an analog signal representing a desired extinction coefficient $b_{scat}$ by any one of a number of apparatus, including an averaging circuit, or a second counter and a D-to-A converter. Dark current compensation, if necessary, is effected by either subtracting a fixed value, or a value dependent on some environmental variable, from the measured value of $b_{scat}$, or by utilizing a reversible counter apparatus and light source apparatus.

Variations of this nephelometer are also described, including an instrument for automatically compensating for the component of $b_{scat}$ due to Rayleigh scatter by gases, an instrument which is sensitive to a plurality of wavelengths, and a self-calibrating instrument which is adapted for the measurement of total light scatter and back scatter at a plurality of wavelengths.

46 Claims, 14 Drawing Figures

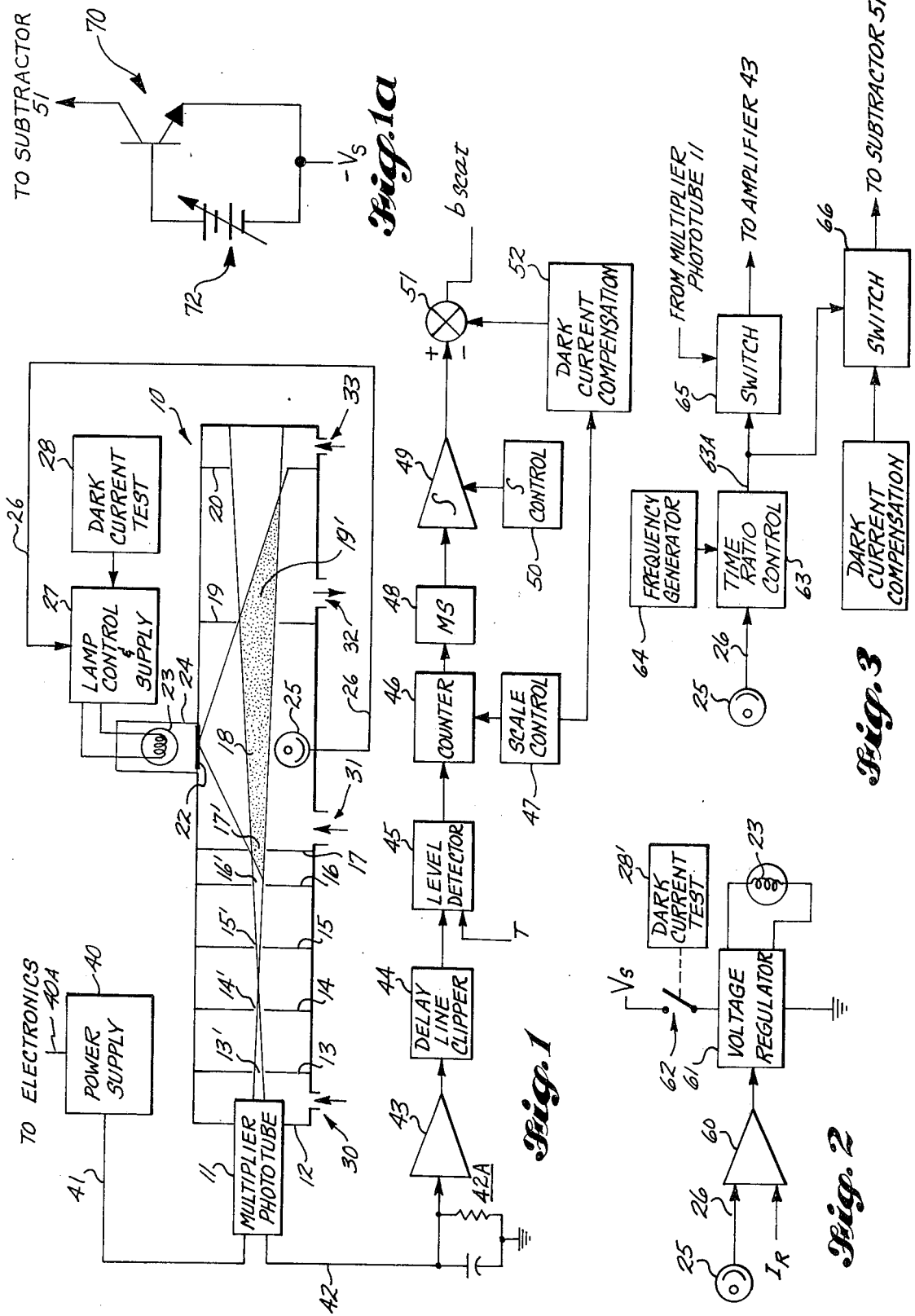

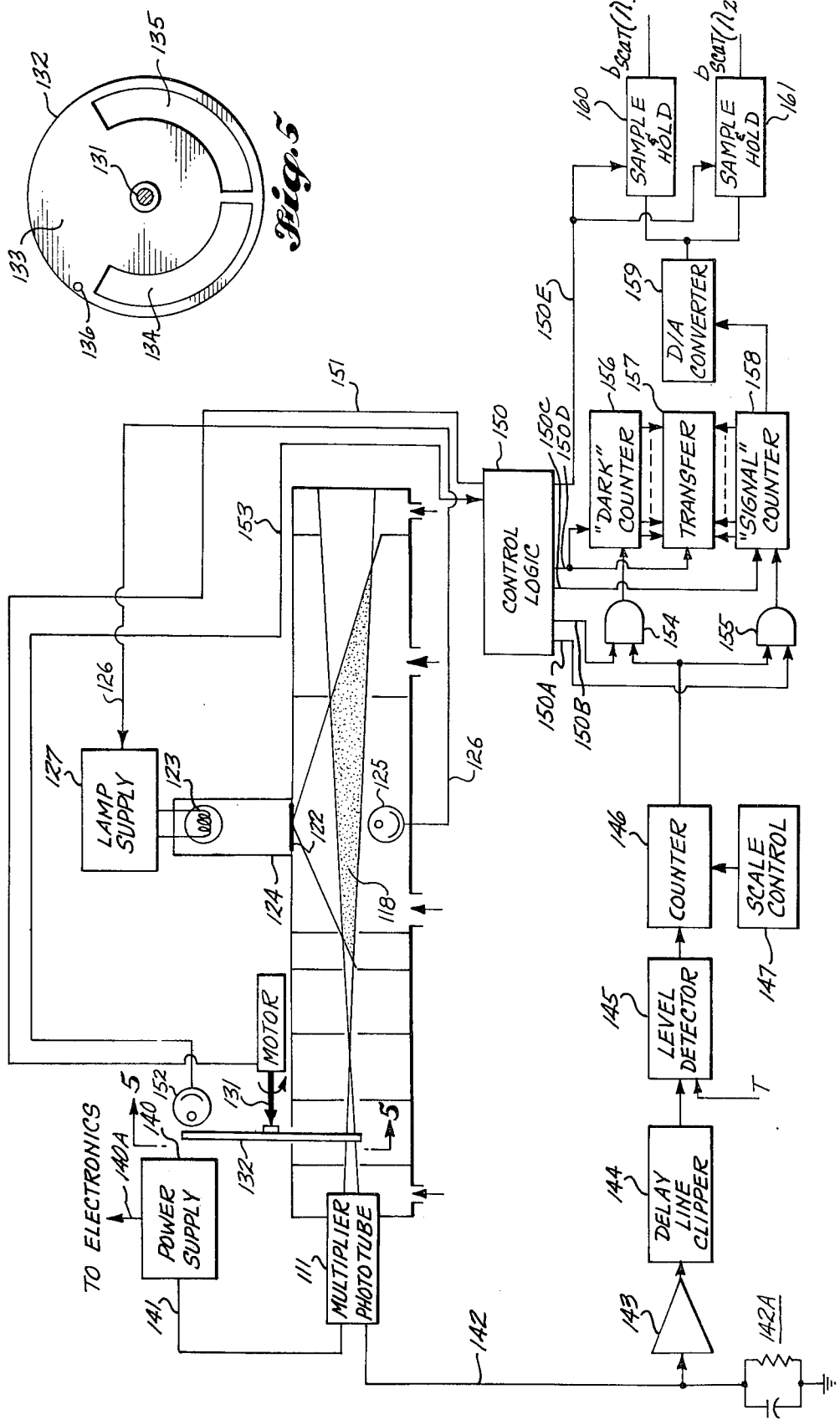

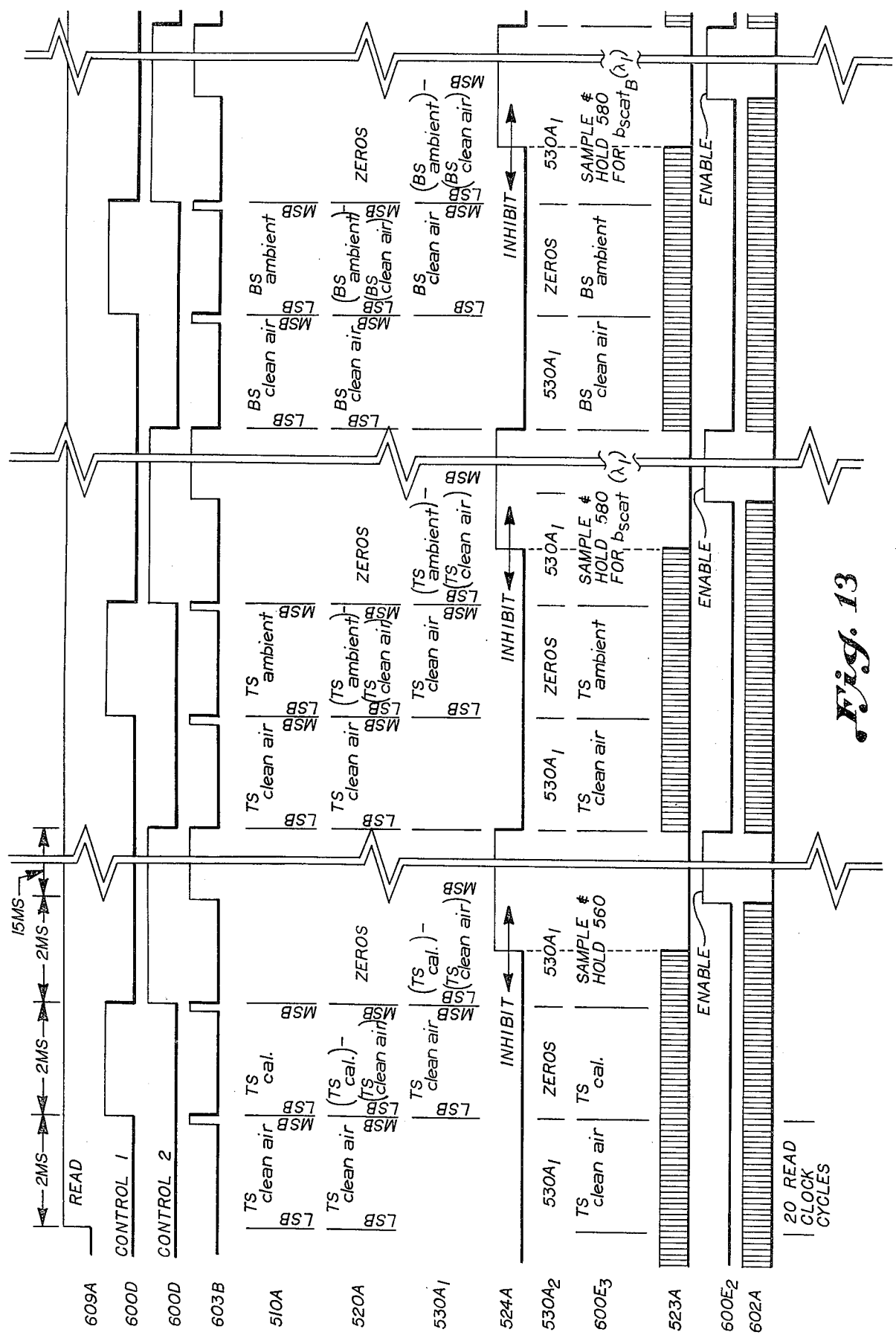

PHOTON-COUNTING INTEGRATING NEPHELOMETER

CROSS-REFERENCE TO RELATED APPLICATIONS

This application is a continuation-in-part of copending U.S. application Ser. No. 435,734, filed Jan. 23, 1974 now abandoned, which in turn is a continuation of application Ser. No. 351,609, filed Apr. 16, 1973, and now abandoned.

FIELD OF THE INVENTION

This invention relates generally to apparatus for monitoring atmospheric aerosols, and more particularly, to an improved integrating nephelometer using a photon-counting technique for light scatter detection.

BACKGROUND OF THE INVENTION

The spatial distribution, including the kind and quantity of atmospheric pollutants in the vicinity of urban complexes or otherwise has been difficult to evaluate. These pollutants generally comprise an aerosol, which may be defined as a colloidal suspension of liquid or solid particles in the air.

The visual quality of air, including visual range and color, is related to air pollution by an atmospheric aerosol. Increases in atmospheric aerosol provide a degradation in visual quality which manifests itself in reduced visibility through the atmosphere.

In order to have an exact criterion of visual quality and to be able to measure the kind and quantity of atmospheric aerosol, the extinction coefficient due to light scattering may be measured.

The light scattering coefficient is defined in "A New Instrument for Evaluating the Visual Quality of Air" by Ahlquist and Charlson, Journal of the Air Pollution Control Association, Volume 17, Number 7, July 1967. The light scattering coefficient may be determined by implementing the following attenuation equation:

$$I/I_o = e^{-bx}$$

where:
   $I_o$ = intensity of light prior to entering an atmospheric path.
   $I$ = intensity of light after passage through an atmospheric path of distance $x$.
   $b$ = extinction coefficient.
   The quality $b$, is made up of two components, $$b = b_{abs} + b_{scat}$$

where:
   $b_{abs}$ = extinction coefficient due to absorption of light by particles or gases.
   $b_{scat}$ = extinction coefficient due to scatter of light by particles or gases.

In general, it is possible to assume that $b = b_{scat}$ unless, of course, substantial quantities of light absorbing gases (e.g., $NO_2$) or particles (e.g., soot) are present. For most atmospheric aerosols, $b_{scat}$ is estimated to be about 3 to 100 times larger than $b_{abs}$. Integrating nephelometers have been built for measuring the scattering component of extinction coefficient, $b_{scat}$. Such devices optically integrate light scattered in all angles by the aerosol particles to obtain a value of $b_{scat}$ and are to be distinguished from devices which measure light scattering only at a discrete angle or angles.

The term "scattering angle" as used hereinafter is defined as the angle included between the line projected from a light source and extending beyond a particle, and a line comprising the direction of light from the source which is scattered by the particle receiving light from the particle. A scattering angle of 0° is defined as transmitted light, and a scattering angle of 180° is defined as reflected light. The terms "light scatter," "total scatter," and "light scattering" as used hereinafter are thus defined as that measured by taking the integral of scattered light over all scattering angles.

The term "back scatter" as used hereinafter is defined as that measured by taking the integral of scattered light over scattering angles in the range of 90° to 180°.

The advantage of the nephelometer over other devices for measuring the visual quality of air is that the nephelometer takes a reading of the coefficient $b_{scat}$ at what may be considered a point in space and in time. Since the integrating nephelometer may be designed to provide an output proportional to the extinction coefficient due to light scattering $b_{scat}$, it is then a simple matter to relate this coefficient to spatial distribution of atmospheric aerosol by taking a plurality of readings at different points in space and time. It has been shown that the extinction coefficient due to light scattering can also be simply related to both visual range and to the mass of aerosol per volume of air by simple formulas.

An integrating nephelometer described in U.S. Pat. No. 3,563,661, Feb. 16, 1971, by Robert J. Charlson and Norman C. Ahlquist, which is also assigned to the assignee of the present invention, is particularly adapted for highly sensitive, accurate and correlatable monitoring of atmospheric aerosol. This device provides an electrical output signal which is proportional to the measured value of the extinction coefficient due to light scattering, or $b_{scat}$, for a given aerosol sample.

The integrating nephelometer described in the aforementioned Charlson et al patent includes a sample chamber, an inlet and an outlet for introducing and removing a sample of the aerosol into and from the chamber, a light source which produces a light pulse of high intensity and having a cosine emission characteristic, and means situating the light source so that the maximum of the cosine emission characteristic is positioned at right angles to the axis of a cone of observation. A measuring photomultiplier tube is situated in the housing to receive the portions of the light pulse which are scattered by the aerosol sample and which pass through the vertex of the cone of observation. A reference photoelectric detector receives light directly from the source, and a divider circuit takes the ratio of the output from the measuring photomultiplier tube and the output of the reference detector. A trigger device and sampling means coordinates the production of the light pulse from the light source and sampling of the output from the divider circuit to provide a signal proportional to the desired extinction coefficient $b_{scat}$.

The combination of a light source of high intensity such as a flashlamp, plus pulsed operation thereof, when combined with use of both a measuring and reference photodetector, more commonly referred to as a two-beam optical system, provides an improvement in sensitivity over previous integrating nephelometers by a factor of approximately 20, resulting in a detection limit for $b_{scat}$ of less than $1 \times 10^{-5}$ m$^{-1}$ (per meter). In addition, an instrument constructed according to the preferred embodiment of the Charlson et al patent is rugged and readily adaptable to hostile environments. Because of its versatility and sensitivity, this prior integrating nephelometer is adaptable to obtaining information about atmospheric aerosols which was heretofore unrecognized or unmeasurable by previous instruments.

An integrating nephelometer of this type lends itself to classification of aerosols by measurement of the extinction coefficient due to light scattering. In addition, such a nephelometer is adaptable to instantaneous measurements on aerosol samples from which the present characteristics thereof which are related to air pollution, such as visual range and mass concentration, can be determined, and from the future characteristics or effects of the aerosol upon the atmosphere can be predicted.

An instrument constructed according to the teachings of the above-identified Charlson et al patent has proved disadvantageous in some respects, however. For example, the circuitry involved is complex and requires many components, thereby resulting in a fairly expensive device. The flashlamp used in most embodiments is also an expensive item, and has proven to present problems with respect to instrument stability because of variations in flashlamp intensity. While the two-beam optical system and the timing and sampling techniques used in the instrument compensate for most of the short-term variations in flashlamp intensity, and additionally provide noise reduction so as to increase the instrument sensitivity as previously described, they have not proven adequate to compensate for long-term drift in the instrument. In addition, short-term noise resulting from variations in gain and changes in dark current of the measuring photomultiplier tube has limited the sensitivity and stability of the instrument.

An instrument constructed according to the preferred embodiment of the Charlson et al patent utilizes analog circuits, and, as such, has a restricted dynamic range. That is, in some instances, the extinction coefficient $b_{scat}$ might vary from $10^{-2}$ to $10^{-7}$ $m^{-1}$ in a short time period and would be measureable only by changing the range sensitivity of the instrument.

Furthermore, the discontinuous operation of such an instrument, in which measurements are taken during only certain intervals of a measuring interval, decreases the signal-to-noise ratio over that obtainable, were continuous monitoring of the extinction coefficient $b_{scat}$ possible.

It is therefore an object of this invention to provide an improved integrating nephelometer which has a greatly extended dynamic range for the monitoring of the extinction coefficient due to light scattering of atmospheric aerosols.

It is another object of this invention to provide such an improved integrating nephelometer which is highly sensitive and which has an improved signal-to-noise ratio over previous integrating nephelometers.

It is yet another object of this invention to provide such an improved integrating nephelometer which is less expensive than previous integrating nephelometers.

It is still another object of this invention to provide such an improved integrating nephelometer which is capable of providing highly accurate measurement of the extinction coefficient due to light scattering of atmospheric aerosols at a plurality of wavelengths over an extended period of time.

It is a further object of this invention to provide such an improved integrating nephelometer which is self-calibrating at periodic intervals to further increase the sensitivity and stability of the instrument over previous integrating nephelometers.

It is yet another object of this invention to provide such an improved integrating nephelometer which can measure not only the extinction coefficient due to light scattering of atmospheric aerosols, but also the back scatter component of such extinction coefficient, at a plurality of wavelengths.

It is still a further object of this invention to provide such an improved integrating nephelometer which utilizes digital data processing techniques to effect extinction coefficient measurements.

SUMMARY OF THE INVENTION

Briefly, these objects and the further objects and advantages described hereinafter are achieved by replacing the flashlamp or pulsed light source of the prior integrating nephelometer with a continuously operating light source, such as a bulb including a tungsten incandescent filament. A photondetecting means capable of detecting single photons of scattered light includes in one embodiment, a measuring photodetector or photomultiplier tube, a pulse stretching network, an amplifier, and a level detector and is operable to produce one output pulse for each photoelectron and "dark current" electron produced by the photomultiplier tube's photocathode which reach the photomultiplier tube's anode. The output pulses from the photon-detecting apparatus are supplied to a scale counter which provides an output pulse for a predetermined number of input pulses, and whose division ratio is adjustable to provide instrument sensitivity or scale control.

In a first embodiment, the output of the scale counter triggers a monostale multivibrator whose output is supplied to an averaging circuit whose output comprises an analog signal proportional to the rate of detected photoelectrons and the "dark current" of the measuring photomultiplier tube, and which is supplied to one input of a subtractor circuit, to whose other input is supplied a correction signal proportional to the estimated "dark current." The resultant output of the subtractor circuit is proportional to the desired extinction coefficient due to light scattering, $b_{scat}$.

The light source intensity is regulated independently by a lamp control and supply circuit which receives its input from a second photodetector which looks directly at the light source output.

In a second embodiment, the output of the photon-detecting apparatus is again supplied to a scale counter whose shaped output is supplied to a reversible counter apparatus. Means are provided for turning the light source off and observing the cone of observation during a first period of time during each measurement cycle, during which time the reversible counter counts in one direction. Means are then provided for turning the light source on for a second period of time. During the second period, having a duration equal to that of the first period, the reversible counter counts in an opposite direction. At the end of the second period, the resultant count in the counter is directly proportional to photoelectrons resulting from light scattering, and is compensated for the "dark current" of the photomultiplier tube. The digital number in the counter is then converted into analog form by a D-to-A converter and supplied to output circuitry as the desired extinction coefficient $b_{scat}$.

In a third embodiment, the nephelometer measuring chamber is alternately supplied with a sample containing an atmospheric aerosol whose extinction coefficent is to be measured, and with clean, aerosol-free air whose physical parameters, such as temperature and relative humidity, are similar to those of the sample. The light source is maintained continuously on and a reversible counter is caused to count in one direction when the sample is within the measuring chamber, and to count in an opposite direction when clean, aerosol-free air is within the chamber, both for identical periods of time. At the end of the second counting period, the contents of the counter represents the extinction coefficient $b_{scat}$ due to light scattering by particles, and is compensated for: (a) noise, including "dark current"; (b) the extinction coefficient $b_{scat}$ due to Rayleigh light scatter by gases; and (c) light scatter by the walls of the instrument.

The invention as described also includes various means for altering the wavelength sensitivity of the nephelometer during measurement cycles so that the wavelength dependence α of the extinction coefficient $b_{scat}$ due to light scattering may be determined.

In a fourth embodiment, the output pulses from a plurality of photon-detecting apparatus, one for each wavelength to be investigated, are accumulated and supplied to a digital memory under control of a timing and control apparatus. In a calibration cycle of operation, the nephelometer measuring chamber is supplied with clean, aerosol-free air. At the end of a first predetermined "clean air" interval, the number of photon counts accumulated for each wavelength are stored in the digital memory. Subsequently, a white calibrating object designed to produce a known value of the extinction coefficient $b_{scat}$ is inserted into the cone of observation in the nephelometer measuring chamber and "calibrate" photon counts for each wavelength are accumulated and stored for a second time interval equal in duration to that of the first time interval.

In a measurement mode of operation, the nephelometer measuring chamber is continuously supplied with atmospheric aerosol whose extinction is to be measured. Each measurement cycle is divided into successive accumulating and read cycles.

During each accumulating cycle, "ambient" photon counts from the photon-detecting apparatus are accumulated and stored for each wavelength.

During each read cycle the stored "clean air" counts for each wavelength are subtracted from the "ambient" photon counts for each wavelength accumulated during the preceding accumulating cycle. The resultant "measurement" signals are therefore compensated for Rayleigh scatter, dark current, and light scatter by the walls of the instrument. Also, the stored "clean air" counts for each wavelength are subtracted from the "calibrate" counts for each wavelength to obtain calibrating signals which represent the extinction coefficient of the white calibrating object, as compensated for Rayleigh scatter, dark current, and instrument wall light scatter. Then the resultant "measurement" signal for each wavelength is divided by the corresponding calibrating signals for each wavelength to obtain an output signal proportional to $b_{scat}$ which is compensated for long-term drift in the measuring photomultiplier tubes and in the continuous light source.

A modification involves the use of a shutter device which is alternately moved in and out of position in the nephelometer measuring chamber for successive time intervals of equal duration during each measurement cycle. When in position the shutter allows measurement of back scatter by blocking light from the light source over scattering angles in the range of 0° to 90° from reaching the cone of observation of the measuring multiplier phototube.

BRIEF DESCRIPTION OF THE DRAWINGS

The invention can perhaps be best understood by reference to the following portion of the specification, taken in conjunction with the accompanying drawings in which:

FIG. 1 is a schematic sectional view of one embodiment of the improved integrating nephelometer, including a combined schematic and block diagram of the optical and electronic systems thereof;

FIG. 1a is a schematic diagram illustrating one embodiment of the dark current compensation current in FIG. 1;

FIG. 2 is a block diagram illustrating one embodiment of the lamp control and supply circuit in FIG. 1;

FIG. 3 is a block diagram illustrating another embodiment of the lamp control and supply circuit in FIG. 1;

FIG. 4 is a schematic sectional view of a second embodiment of the improved integrating nephelometer, including a combined schematic and block diagram of its optical and electronic systems including a reversible counter;

FIG. 5 is a side elevation view of the filter wheel used in the embodiment of FIG. 4;

FIGS. 11, 12 and 13 are timed diagrams illustrating the operation of the fourth embodiment detailed in FIGS. 8, 9 and 10.

DESCRIPTION OF A PREFERRED EMBODIMENT

Figure 6:
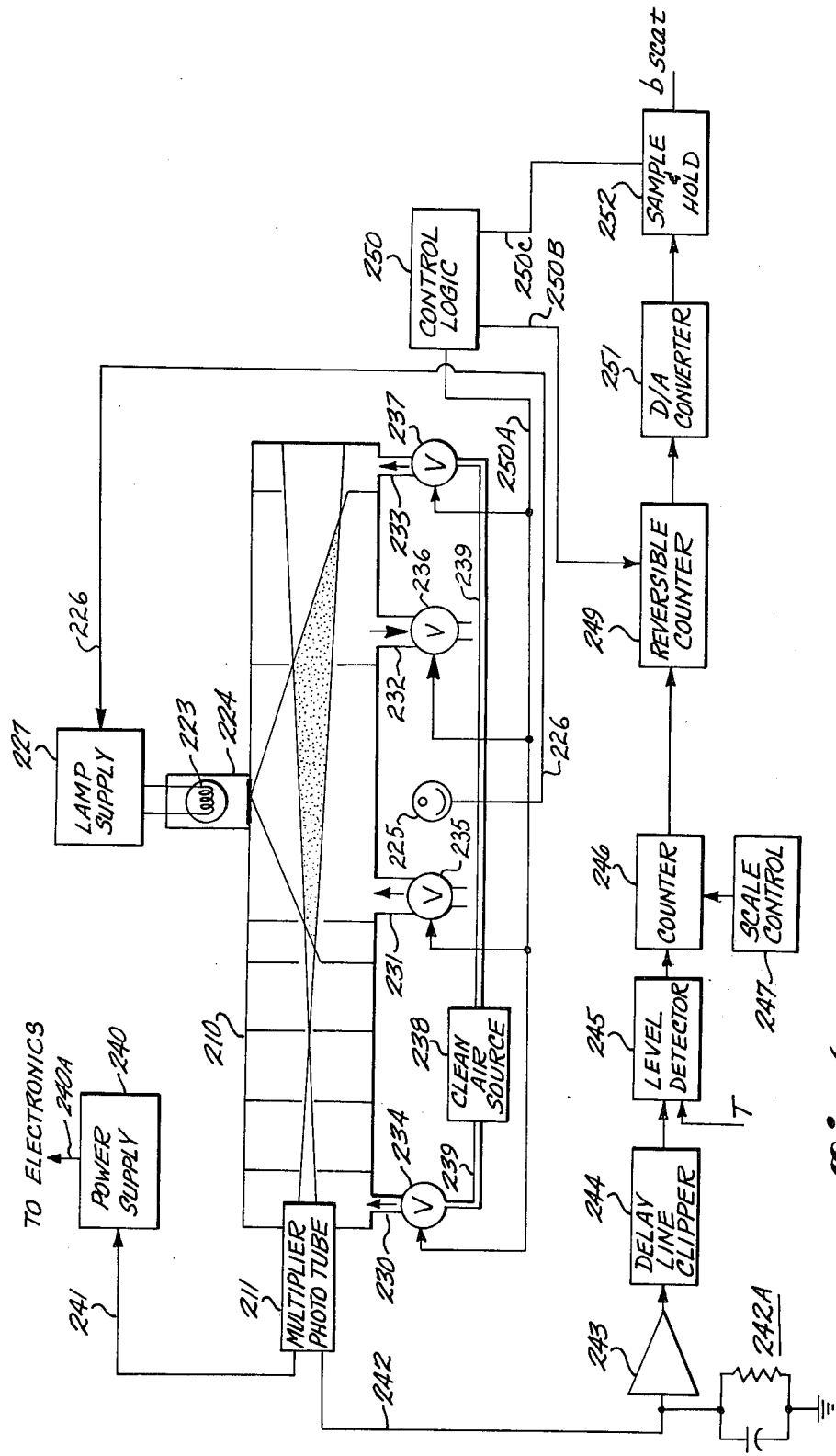
FIG. 6 is a schematic sectional view of a third embodiment of the improved integrating nephelometer, including a combined schematic and block diagram of its optical and electrical systems and illustrating an alternate sample and clean air source control means.

With reference now to FIG. 1, the optical system of the nephelometer is disposed in a container 10 having a tubular or other shape which may be of aluminum or other suitable material. A multiplier phototube 11, such as a commercially available EMI 9558C tube, or an RCA 931B phototube, is mounted in the forward end 12 of the container 10.

A plurality of plates, such as discs 13, 14, 15, 16 and 17, are disposed within the container 10 and are arranged to define a collimator and light trap. The discs 13, 14, 15, 16 and 17 define a series of apertures 13', 14', 15', 16' and 17' which are optically aligned with the phototube 11. A cone of observation 18 is defined by the disc 13 and the disc 16 and does not intersect the edges of apertures 14', 15', and 17'. Discs 14, 15 and 17 serve as light traps and cast shadows on any surfaces seen by the phototube 11. The inside surfaces preferably are all coated with flat black paint to further reduce the effect of any reflected light.

The air sample is illuminated by a light source 23 comprising a lamp and an opal glass diffuser or window 22 disposed in a suitable housing 24 and located in the center section of the tubular container 10. The lamp 23, may, for example, consist of a tungsten filament incandescent bulb with a reflector, such as a commercially available DNF 150 watt, 21 volt bulb which produces a cosine emission characteristic by means of the opal glas diffuser 22. The diffuser 22 also forms a seal to the sample chamber. The fact that this geometry integrates over all scattering angles has been illustrated in the book "*Vison Through the Atmosphere*" by W. E. K. Middleton (1963).

A second series of plates, typified by discs 19 and 20, are disposed in the rear portion of the tubular container 10 and are separated from the discs 13–17 by the central section of container 10. The disc 19 defines an aperture 19' which further defines the sample volume or cone of observation 18. The remaining discs, such as disc 20, serve as light traps and cast shadows on surfaces seen by the phototube 11.

An inlet duct 31 is provided for admitting air or other fluid to be sampled into the central sampling section and an outlet duct 32 is provided for discharging the sample air after passing through the central section. Airflow through the system is on a continuous basis. Clean purge air and a source of air for nephelometer calibration are obtained by two auxiliary inlets 30, 33 which are operated in conjunction with suitable valve means, not illustrated, during calibration.

The primary standard for nepehlometer calibration is the Rayleigh scattering of particle-free air of other particle-free gases such as helium, $CO_2$, chlorodifluoromethane ($CHClF_2$), and dichlorodifluoromethane ($CCl_2F_2$). Rayleigh scattering is typically one portion of the total coefficient $b_{scat}$ measured by the instrument, for example, $b_{scat} = b_{scat(Rayleigh)} + b_{scat(particles)}$. Initial calibration of the nephelometer is made in the laboratory using controlled sources of the above-noted particle-free gases.

For field calibration, the extinction coefficient $b_{scat}$ of particle-free air is a known value equal to a $b_{scat}$ of zero, whereas the extinction coefficient $b_{scat}$ of $CCl_2F_2$ is a known but relatively higher value. Thus, two values of the extinction coefficient $b_{scat}$ can be provided for field calibration, if the above-noted gases are available, or if material or devices which provide $b_{scat}$ signals known in magnitude relative to those of these gases can be obtained. For example, the first value of $b_{scat}$ can be checked by passing the purge air provided through inlets 30 and 33 through glass fiber filters, and the second value of $b_{scat}$ can be checked by interposing a truly white object, such as one coated with magnesium oxide, in the cone of observation 18.

The electronic system includes a power supply 40 having a low voltage output $V_s$, available on lead 40A, for the electronic circuit hereinafter to be described, including a lamp control and supply circuit 27 for the lamp 23, and a high voltage output suitable for application to the multiplier phototube 11 through a lead 41.

The output of multiplier phototube 11 is connected by a lead 42 to the input of a high-speed amplifier 43. An R.C. circuit 42A is connected from lead 42 to reference potential. The signal on lead 42 comprises pulses due to individual electrons emitted from the photocathode of the multiplier phototube 11, pulses from individual electrons thermally emitted from points within the chain of dynode electrodes in the multiplier phototube 11, and leakage current between elements in the multiplier phototube 11. In this signal, only the discrete pulses resulting from individual electrons emitted from the photocathode contain useful information and the other pulses and currents comprise noise.

The photon-detecting apparatus including an R.C. circuit 42A, a high-speed amplifier 43, a delay line clipper 44, and a level detector 45, operates to eliminate those noise signals from the signals present on line 42.

Specifically, R.C. circuit 42A and high-speed amplifier 43 are designed to provide a train of output pulses to delay line clipper 44 which have a fast rise time and a slow fall time, but which are otherwise amplified versions of the input pulses on line 42. As the input pulses have a fairly short duration, on the order of 5 nanoseconds, it is good practice to lengthen these pulses, by operation of R.C. circuit 42A, to reduce variations in pulse height caused by transit time variation through the electron multiplier structure of the multiplier phototube 11. The function of delay line clipper 44 is to reference each pulse from amplifier 43 to a common DC reference potential, or to effectively stabilize its reference level, so that they can be effectively operated on by the level detector 45, and to square each pulse by shortening the fall time portion thereof. The function of clipper 44 could also be provided by a parallel R.L.C. circuit connected from the output of amplifier 43 to reference potential.

Because photoelectrons and "dark current" electrons emitted from the photocathode of the multiplier phototube 11 have been amplified by all the dynode electrodes in the phototube 11, the resultant output pulses appearing on line 42 have a larger amplitude than the noise pulses and signals, which have passed through only a portion of the dynode electrode stages. Therefore, the level detector 45 is provided with an input threshold T which is set at a level sufficient to allow the level detector 45 to provide an output pulse for each input pulse thereto which is a result of a photoelectron or "dark current" electron. However, level detector 45 will not provide an output pulse for the lower-magnitude pulses and signals resulting from noise.

Therefore, the photon-detecting apparatus including R.C. circuit 42A, amplifier 43, delay line clipper 44 and level detector 45 effectively discriminates against noise pulses and signals of the kind previously described and provides one output pulse on the out-put of level detector 45 for each electron emitted from the photocathode of the miltiplier phototube 11 which travels through the electrode structure of the phototube 11 to its anode or output.

The electrons result from a) photons incident on the multiplier phototube 11 arising out of 1) light scatter by particles within the cone of observation 18, 2) light scatter by the gas within the cone of observation 18 (Rayleigh scatter), and 3) unwanted reflections from the sides and other interior surfaces of the container 10, and, b) thermal emission from the photocathode of multiplier phototube 11, at a rate dependent on temperature. The thermal emission source of electrons is conventionally referred to as a "dark current."

If it is desired to obtain an output signal $b_{scat}$ which is proportional to the scattering due to particles only, the components due to Rayleigh scatter of gases and due to unwanted reflections from interior surfaces which are present at the output of level detector 45 may be eliminated by the equivalent of a simple subtraction process, as it may be assumed that for most cases, Rayleigh scatter and "background scatter" due to unwanted reflections are constant.

However, as the "dark current" is very dependent on temperature, its effect cannot be so easily compensated for and therefore special circuitry is herein provided.

Referring now back to FIG. 1, the output of level detector 45 is coupled to the input of the scale counter 46 which may have a predetermined number of ranges. In one embodiment, counter 46 had divide by 32, divide by 64, divide by 128 or divide by 256 ranges. That is, counter 46 is operative to provide an output pulse for every predetermined number of input pulses thereto, dependent on the range to which it has been set. This range is established by a scale control circuit 47 which includes a manually adjusted switch, not illustrated, for scale selection.

Counter 46 performs two functions. First, by providing an output signal for only a predetermined number of input pulses thereto, it "averages" short term variations in the rate of detected photoelectrons which might otherwise be a source of error. Second, by its adjustable range feature, counter 46 allows the instrument to be set at various scales of sensitivity.

Each output pulse from counter 46 is shaped by a monostable multivibrator 48 into a corresponding output pulse of predetermined height and duration, which in turn is supplied to the input of an averaging amplifier 49 whose averaging time constant is controlled by an averaging control 50 connected thereto. In effect, averaging amplifier 49 provides a simple digital-to-analog conversion of the pulse rate provided at the output of multivibrator 48 into a corresponding analog signal. Averaging control 50 allows adjustment of this averaging to correspond with the range and scale that has been set into counter 46 by scale control 47.

The output analog signal from averaging amplifier 49 therefore is proportional to the desired extinction coefficient $b_{scat}$, due to Rayleigh scatter, particle scatter and unwanted reflections, plus a component resulting from the dark current.

The signal on the output of averaging amplifier 49 is supplied to one input of a subtractor circuit 51 which also receives an input from a dark current compensation circuit 52. In a working mode, dark current compensation circuit 52 comprised a manually adjustable potentiometer providing an adjustable DC signal to the input of subtractor circuit 51. To establish a value for the output from the dark current compensation circuit 52 for a given scale of the instrument, and therefore for a given range of scale counter 46, the lamp control and supply circuit 27 also receives as an input the output of a dark current test circuit 28. Actuation of dark current test circuit 28, by manual or automatic means not illustrated, provides a signal to lamp control and supply circuit 27 to cause lamp 33 to be turned off. Under this condition, the only signal that is present at the output of averaging amplifier 49 is that which results from dark current. Therefore, the potentiometer within dark current compensation circuit 52 is manually adjusted until the output signal from subtractor circuit 51 is zero. For subsequent operation, then, when the lamp 23 is again turned on by de-actuation of dark current test circuit 28, the output signal from subtractor circuit 51 is compensated for dark current and is directly proportional to the desired extinction coefficient $b_{scat}$.

It will be noted that dark current compensation circuit 52 also receives an input from scale control circuit 47 which adjusts the output signal from dark current compensation circuit 52 by a fixed amount equal to a ratio of the counter range of counter 46 at which counter 46 is operating, and the range at which the dark current compensation circuit 52 was set by operation of dark current test circuit 28, as previously described. In a working model, a network of series-connected resistors was connected in series with the potentiometer between the supply $V_s$ and reference potential, and switching between the series resistors was accomplished in response to the signal from scale control circuit 47.

The electronic system of the integrating nephelometer of FIG. 1 can be repeatedly adjusted for dark current compensation by periodic actuations of the dark current test circuit 28 and by concurrent manipulations of the dark current compensation circuit 52 to provide a zero output from subtractor circuit 51.

Another embodiment of the dark current compensation circuit 52 is illustrated in FIG. 1a. In this embodiment, a transistor 70, which is preferably a silicon transistor, has its emitter connected to a negative supply voltage $-V_s$ and its collector to subtractor 51. An adjustable biasing voltage source 72 is connected between the emitter and the base of transistor 70 and is therefore in parallel with the base-emitter junction thereof.

As previously noted, dark current is very dependent upon temperature. For most commercially available multiplier phototubes, it has been found that the dark current varies exponentially with temperature. It is known that the collector current in a transistor is a function of temperature, and it has been found that if a constant voltage is supplied across the base-emitter junction of the transistor, the collector current thereof varies exponentially with temperature, as long as the transistor is run in its linear region of operation.

Therefore, the circuit in FIG. 1a can be advantageously used to provide a continuous compensation of the output from the dark current compensation circuit 52 in order to avoid the repeated adjustments as previously described. In particular, dark current test circuit 28 is actuated as previously described to cause lamp 23 to be turned off. Then, adjustable biasing voltage source 72 is manually adjusted until the output signal from subtractor circuit 51 is zero. At this time, dark current compensation has been effected and will continue to be effected thereafter for changes in the dark current which are temperature related, as the collector current of transistor 70, and therefore the dark current compensation signal, varies in a manner similar to the temperature-related changes in dark current.

In order to obtain stable operation of the nephelometer in FIG. 1, the light intensity of the output from lamp 23 must be essentially constant. Accordingly, a photodetector 25 is disposed within container 10 to receive light from lamp 23 through opal glass diffuser 22 and which in turn provides an output signal on line 26 to an input of lamp control and supply circuit 27.

One embodiment of lamp control and supply circuit 27 is seen in FIG. 2, in which the signal on line 26 from phototube 25 is supplied to one input of differential amplifier 60. The other input of differential amplifier 60 is supplied with a reference signal $I_R$ representing a desired constant light intensity output for lamp 23. A resultant error signal on the output of differential amplifier 60 is supplied to the control input of a conventional voltage regulator 61 which is connected to reference potential and to the biasing voltage supply $V_s$ through a pair of relay contacts 62 which are normally closed. Voltage regulator 61 modifies the supply voltage $V_s$ in response to the output signal from amplifier 60 to control the voltage applied across the lamp 23. It is of course well known that control of the voltage across a tungsten filament incandescent bulb controls the bulb's light intensity. By this simple feedback system, the light intensity output of lamp 23 is maintained approximately constant.

The contacts 62 are connected to a relay coil, not illustrated, within dark current test circuit 28. Upon actuation of dark current test circuit 28, the contacts 62 are opened to remove the biasing voltage supply $V_s$ from the voltage regulator 61, and therefore to turn the lamp 23 off.

An apparatus for directing compensating for variations in light source intensity is seen in FIG. 3. In this embodiment, the duty cycle, or ratio of on-off times, of the output signal from multiplier phototube 11 is varied in proportion to the reciprocal of the output light intensity. Specifically, the output lead 26 from photodetector 25 is connected to the input of a conventional time ratio control 63 which also receives an input from a frequency generator 64, which may be a source of 60 Hz signals. Time ratio control 63 is operative to provide a series of output pulses on its output terminal 63A which occur at the frequency of frequency generator 64 and whose "on" duration are directly proportional to the reciprocal of the light intensity, as represented by the signal from photodetector 25 on line 26. These pulses are supplied to a switch 65 connected between the multiplier phototube 11 and amplifier 43.

Since phototube 11 is therefore on for only a portion of an arbitrarily defined measurement period, the pulses on line 63A are likewise supplied to a switch 66 connected between the dark current compensation circuit 52 and the subtractor circuit 51.

As previously described in the aforementioned Charlson et al patent, an integrating nephelometer of the type described has a broad band response to light scattering. To correct that broad band response to a wavelength which approximates the peak sensitivity of the human eye (approximately 525–550 nm), and therefore to obtain results which are meaningful with respect to visual quality, the multiplier phototube 11 may be provided with a Wratten-type 58 filter and a type S-20 photocathode in the case where the phototube is the EMI 9558C, to provide a wavelength sensitive band of 525 nm, ± 25 nm. For less expensive instruments, a type S-4 or S-11 photocathode would be sufficient.

Because the embodiment in FIG. 1 allows detection and measurement of individual photons on a continuous basis, its sensitivity and stability over the prior integrating nephelometers, including the type described in the aforementioned Charlson et al patent, is improved by a factor of 10 to 20. The embodiment in FIG. 1 is advantageous if an observer can be present to periodically correct the dark current compensation. With the particular multiplier phototubes previously mentioned, especially the RCA 931B, dark current is minimized. Accordingly, its effect on nephelometer accuracy on all but the most sensitive ranges is small. Furthermore, ambient temperature changes are usually long-term so that recalibration of the dark current compensation at hourly intervals, for example, may be sufficient.

In those situations where a completely automated instrument is desired, but with somewhat poorer signal-to-noise ratio than described in FIG. 1, the embodiment in FIGS. 4 and 5 may be used.

The nephelometer optical system, including a tubular or other shape container and a plurality of spaced, interior plates or discs, is identical to that illustrated in FIG. 1 and is generally designated at 110. Also included is a lamp 123, which again may comprise a tungsten filament incandescent bulb, which is situated in a housing 124. The light intensity of lamp 123 is monitored by a photodetector 125 situated in container 110 whose output, on a line 126, is supplied to a lamp supply circuit 127, which controls the voltage across lamp 123 in response to the monitored light intensity. Lamp supply circuit 127 may be similar in construction to the lamp control and supply circuits illustrated in FIGS. 2 and 3, with the exception that in FIG. 2, the dark current test circuit 28 and associated relay contacts 62 are eliminated, and in FIG. 3, the averaging amplifier 64 and dark current threshold circuit 52' are eliminated.

Light from lamp 123 is incident upon an opal glass diffuser 122, which is identical to diffuser 22 in FIG. 1, and thence into the central or sample section of the nephelometer 110.

The cone of observation 118 in nephelometer 110 is monitored by a multiplier phototube 111 which is energized from a power supply 140 with a high voltage supplied on a lead 141. As before, power supply 140 supplies a voltage $V_s$ on a line 140A to the electronic circuitry of the nephelometer. A rotatable filter wheel 132, to be hereinafter described, is interposed in the cone of observation 118 adjacent multiplier phototube 111.

Output signals from the multiplier phototube 111 are supplied on a line 142 to a photon-detecting apparatus comprising an RC circuit 142A, a high gain amplifier 143, a delay line clipper 144, and a level detector 145, which in turn is supplied with a threshold signal T. The photon-detecting apparatus in FIG. 4 operates in an identical manner to that illustrated in FIG. 1, with the result that the signal at the output of level detector 145 comprises a digital pulse train, wherein one pulse is provided for each photoelectron emitted from the photocathode of the multiplier phototube 111.

The signal at the output of level detector 145 is supplied to a scale counter 146 having a plurality of different ranges which are selected under control of scale control circuit 147, in order to average out the input pulse train and to provide desired sensitivity. The output pulse from scale counter 146 are supplied to a dark current compensation apparatus including a reversible counter and a light source control apparatus.

In the light source control apparatus, the filter wheel 132 is coupled to the output shaft of a motor 130 by a flexible drive means 131. Referring now to FIG. 5, filter wheel 132, in one embodiment, is subdivided into three equi-angle portions including an opaque portion 133, a first filter portion 134, and a second filter portion 135. When the opaque portion 134 rotates adjacent phototube 111 in housing 110, all light from lamp 123 is effectively blocked from phototube 111. Positioning of filter portions 134 annd 135 adjacent phototube 111 admits scattered light to phototube 111. One of the filter portions 134, 135 may comprise a transparent material, and the other may comprise a filter material designed to screen out all light but that within a narrow band of wavelengths. Alternately, both the filter portions 134 and 135 may include narrow-band filters. In a working model, filter portions 134 and 135 comprised green and blue filters having wavelengths of 510 nm and 420 nm, respectively.

As described in more detail in the aforementioned Charlson et al patent, measurement of the extinction coefficient $b_{scat}$ at two different wavelengths for the same or similar aerosol allows computation, by simple circuitry, of the wavelength dependence of the extinction coefficient. This wavelength dependence is simply represented by an exponent $\alpha$ in a relationship $b_{scat} \approx \lambda^{-\alpha}$.

The exponent $\alpha$ is useful in atmospheric calculations, including calibration of the visual range and mass concentration scales on an integrating nephelometer, and provides information about the aerosol size distribution.

The motor 130 continuously rotates at a constant speed and is powered by a 110VAC, 60 Hz source, not illustrated. The actual position of the filter wheel 132 is determined by a photodetector 152 which provides an output on a line 153 to control logic circuit 150. Filter wheel 132 includes an aperture 136 therein which allows a synchronized signal to be produced by photodetector 152 on line 153 once each revolution thereof.

The reversible counter apparatus includes first and second AND gates 154, 155 which receive the output pulse from counter 146, and which additionally have as inputs signals appearing on lines 150B and 150A from control logic circuit 150, respectively. The output of AND gate 154 is coupled to the input of a "dark" counter 156, and the output of AND gate 155 is coupled to the input of a "signal" counter 158. "Dark" counter 156 is controlled by a signal appearing on a line 150D from control logic circuit 150, and "signal" counter 158 is controlled by a signal appearing on a line 150C from control logic circuit 150. The "dark" counter 156 and "signal" counter 158 are interconnected by a transfer circuit 157 which is also controlled by the signal on line 150D. The "signal" counter 158 provides an output to a D-to-A converter 159. The output of the D-to-A converter 159 is in turn supplied to first and second sample and hold circuits 160, 161, which are controlled by a signal appearing on line 150E from control logic 150. The signal on the output of sample and hold circuit 160 corresponds to $b_{scat}(\lambda_1)$ or the extinction coefficient within the band of wavelengths established by the first filter portion 134, and the signal on the output of sample and hold circuit 161 corresponds to $b_{scat}(\lambda_2)$, or the extinction coefficient within the band of wavelengths determined by the second filter portion 135.

Control logic circuit 150 includes appropriate means, well known in the art, to cause the apparatus in FIG. 4 to operate as follows.

Assuming that filter wheel 134 is in a position wherein the opaque portion 133 is interposed between the cone of observation 118 and the multiplier phototube 111, the aperture 136 is in alignment with photodetector 152. A synchronized signal is transmitted by photodetector 152 on line 153 to control logic circuit 150. In response, control logic circuit 150 provides an output signal on line 150B and AND gate 154, so that the pulse train output from counter 146 is coupled to the input of "dark" counter 156. Thereafter, for a predetermined period to be determined by the rotation rate of the motor and the output signal provided on line 150B, "dark" counter 156 accumulates the pulse output from counter 146.

Since the lamp 123 is effectively "off" during this time period, the count that has accumulated in "dark" counter 156 at the end of the period is related to the dark current during the period, or the thermally emitted photoelectrons.

At the end of the period, and before the opaque portion 133 is rotated out of the cone of observation 118, the control logic circuit 150 terminates the signal on line 150B and provides a signal on line 150D which causes the contents of "dark" counter 156 to be transferred through transfer circuit 157 into the "signal" counter 158. Then, the motor 130 advances the filter wheel 132 so that the first filter portion 134 is interposed between the cone of observation 118 and the multiplier phototube 111. Shortly thereafter, control logic circuit 150 provides a signal on line 150A to gate 155 so that the pulse output from counter 146 is coupled to "signal" counter 158. Signal counter 158 is of a type designed to count down from an initial value which has been previously transferred into counter 158. Thereafter, "signal" counter 158 counts down from the initial "dark" count for a predetermined period determined by the duration of the signal on line 150A. Since the lamp 123 is effectively "on" during this time, the count that has accumulated in "signal" counter 158 at the end of the period is related to the number of photoelectrons resulting from detected photons, plus the dark current. At the end of the period interval, control logic circuit 150 removes the signal from line 150A.

The period of the signal on line 150A is identical to the period of the signal on line 150B. Since the dark current is essentially constant during the "dark" counting and "signal" counting periods, the net count in "signal" counter 158 at the end of the second period represents only the photoelectrons resulting from detected photons.

Shortly thereafter, control logic circuit 150 provides a signal on line 150C to "signal" counter 158, to transfer its count to the D-to-A converter 159, wherein it is converted into a corresponding analog signal and supplied to sample and hold circuits 160, 161. Then, a signal on line 150E causes the contents to D-to-A converter 159 to be transferred to sample and hold circuit 160 to be stored therein as the desired extinction coefficient $b_{scat}(\lambda_1)$.

Thereafter, the motor 130 continues to rotate wherein filter wheel 132 is caused to move to its next position wherein the second filter portion 135 is interposed between the cone of observation 118 and the multiplier phototube 111. Concurrent with this operation, the contents of the "dark" counter 156 are again transferred into "signal" counter 158 by an appropriate signal on line 150D. When the second filter portion 155 is in place, a signal is again provided on line 150A by control logic circuit 150 to gate 155, so that the signal counting process is repeated for an identical measuring period. At the end of this period, the contents of "signal" counter 158, which are compensated for dark current as aforesaid, are transferred to the D-to-A converter 159, converted into analog form, and, upon the appearance of a signal on line 150E, stored in sample and hold circuit 161 as the desired extinction coefficient $b_{scat}(\lambda_2)$.

Thereafter, the motor 130 continues to advance to its initial position wherein the opaque portion 133 is adjacent multiplier phototube 111. The resultant signal obtained by light transmission through aperture 136 falling on photodetector 152, once supplied to control logic circuit 150, causes counters 156 and 158, and the sample and hold circuits 160, 161 to be reset to their initial states by signals on lines 150C, 150D, and 150E. Thereafter, the cycle that has been previously described is repeated.

It will be recognized by those skilled in the art that although the embodiment of FIG. 4 has been described with respect to a multi-wavelength version, the principles therein extend to a simple broadband nephelometer of the type shown in FIG. 1 wherein the light source is turned off for the "dark" counting period, and is turned on for the "signal" counting period.

With the embodiments in FIGS. 1 and 4, it may be assumed that the Rayleigh scatter component of $b_{scat}$ is constant. Therefore, if an output signal is desired which is proportional only to the component $b_{scat}$ due to scattering by particles, the component due to Rayleigh scatter (and the component due to reflections from the inside surfaces of the nephelometer, or "background" reflections) can be subtracted as a constant. In cases where ambient conditions are rapidly changing, this assumption may lead to errors in measuring small values of the component of $b_{scat}$ by particles, inasmuch as the value of the Rayleigh scatter component is somewhat dependent upon both temperature and pressure. Accordingly, the embodiment illustrated in FIG. 6 may be used to compensate not only for dark current, but also for Rayleigh scatter, and "background" reflections.

With reference now to FIG. 6, the integrating nephelometer optical system 210 is of a type identical to that previously disclosed and includes a lamp 223 disposed in a housing 224. A photodetector 225 is responsive to light from lamp 223 passing through an opal glass diffuser 222, and provides a corresponding output signal on a line 226 to a lamp supply circuit 227 to accordingly regulate the voltage across lamp 223, and therefore the intensity thereof.

A multiplier phototube 211, of a type identical to that previously described, is disposed at one end of the nephelometer 210 and is energized by a high voltage appearing on line 241 from a power supply 240, which additionally provides a biasing voltage $V_s$ on line 240A to the electronic system. The output signal from multiplier phototube 211 appears on line 242 and is applied to a photon-detecting apparatus, including an RC circuit 242A, a high-gain amplifier 243, a delay line clipper 244, and a level detector 245, identical to elements 42A, 43, 44 and 45 previously described. The pulse train on the output of detector 245 is applied to a scale counter 246, whose associated scale control circuit 247 operates in a manner identical to elements 46 and 47 previously described. The output from counter 246 is applied to the input of a reversible counter apparatus 249, which may be similar to that illustrated in more detail in FIG. 4 as including gates 154, 155, counters 156, and 158, and transfer circuit 157. Reversible counter 249 receives control input signals from a control logic circuit 250 on a line 250B, and supplies an output to a D-to-A converter 251 whose analog output signal is connected to a sample and hold circuit 252.

The nephelometer 210 includes a sample air inlet 231 and an outlet 232, in which are disposed a valve 235 and a valve 236, respectively. A source of clean air 238 is provided and connected by a line 239 to valves 234 annd 237 disposed, respectively, in purge air inlets 230, 233 of the nephelometer 210. The positions of valves 234, 235, 236, and 237 are controlled by control signals from control logic circuit 250 via line 250A. Control logic circuit 250 also provides a control signal to sample and hold circuit 252 via line 250C.

The operation of the circuit in FIG. 6 is as follows. At the beginning of a measurement cycle, control logic circuit 250 provides a first control signal on line 250A to open valves 235 and 236, and to close valves 234 and 237. For a predetermined time established by the first control signal, the fluid whose extinction coefficient is to be measured is circulated through the nephelometer 210. Concurrently, control logic circuit 250 provides a signal on line 250B so that reversible counter 249 counts the output pulses from counter 246 in a first direction. At the end of this counting period, or at the termination of the first control signal on line 250A, the count in reversible counter 249 represents components of $b_{scat}$ due to 1) Rayleigh scattering, 2) particle scattering, 3) "background" reflections, and 4) dark current counts.

Thereafter, a second control signal on line 250A causes valve 235 to close, and opens valves 234 and 237, thereby causing clean, filtered purge air to circulate through the interior of the nephelometer 210. At some empirically-determined time after the purge air has begun circulating, sufficient to allow the fluid sample to be completely removed from the interior of nephelometer 210, control logic circuit 250 provides a second control signal on line 250B to reversible counter 249, so that reversible counter 249 counts the output pulses from counter 246 in a direction opposite to that for the previous period. The duration of this second control signal on line 250B is identical to that for the first control signal.

At the end of this second counting period, as determined by the termination of the second control signal, the contents of reversible counter 249 represent only the component of $b_{scat}$ due to particle scattering, if the duration of the periods is chosen to be such that Rayleigh scatter is essentially constant throughout the period. A preferred counting period would have a duration in the range of 30 seconds to 1 minute.

Figure 7:
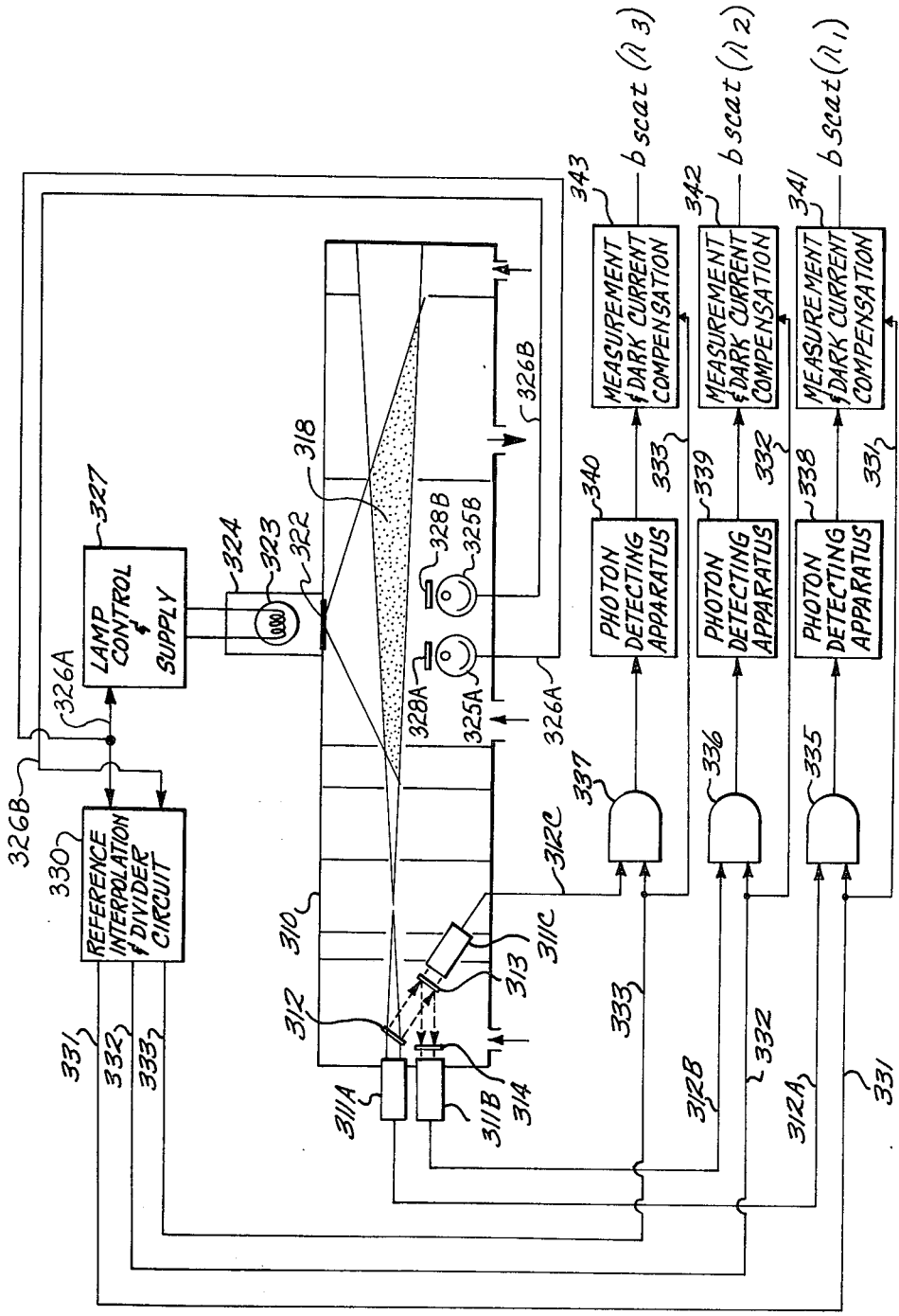
FIG. 7 is a schematic sectional view of the improved integrating nephelometer, including a combined schematic and block diagram of a modification of the optical electronic systems to convert the nephelometer to multi-wavelength applications.

An improved multi-wavelength integrating nephelometer including a photon-detecting apparatus is seen in FIG. 7. As previously mentioned, the multi-wavelength design illustrated in FIG. 4 is disadvantageous in that the light source is switched on and off, and measurement is made through each filter portion for only one-third of each measurement cycle, thereby resulting in a decrease in the signal-to-noise ratio obtainable with the instrument were it to be measuring continuously. In the embodiment of FIG. 7, a single light source is used which is continuously on, and simultaneous measurements are made of $b_{scat}$ at a plurality of different wavelengths.

Referring now to FIG. 7, an integrating nephelometer optical system 310 of the same general type as previously disclosed includes a lamp 323 disposed within a housing 324. Light from lamp 323 is directed upon first and second photodetectors 325A, 325B, in container 310 through an opal glass diffuser 322 and interposed interference filters 328A, 328B also in container 310. Filters 328A and 328B are designed to pass only a narrow band of wavelengths centering about two desired wavelengths $\lambda_1$, $\lambda_3$. Filter 328A may be a blue filter with a center wavelength $\lambda_1$ of 420 nm, and filter 328B may be a red filter with a center wavelength $\lambda_3$ of 600 nm.

The output of photodetector 325A appears on line 326A and is supplied to a lamp control and supply circuit 330. An output 326B from photodetector 325B is also provided to reference interpolator and divider circuit 330. The signal on line 326A acts to regulate the voltage across lamp 323, and therefore the intensity thereof, as previously described. However, regulation of the lamp intensity at a plurality of wavelengths by sensing broadband or narrowband intensity is impractical with a tungsten filament incandescent bulb. For example, changes in voltage applied across the bulb, and thus in filament temperature, to regulate intensity provides a different change in intensity for the various wavelengths being measured. Therefore, the signals on lines 326A, 326B are also supplied to the reference interpolation and divider circuit 330, whose operation will be hereinafter described.

Also provided in nephelometer 310 are a plurality of multiplier phototubes 311A, 311B, and 311C. Multiplier phototubes 311A, 311B and 311C are situated in the forward end of the nephelometer 310. A beam splitter apparatus is provided for directing light from a cone of observation 318 to phototutes 311A, 311B, and 311C. A first filter 312 is supported, by means not illustrated, along the longitudinal axis of the nephelometer 310 in front of phototube 311A and intercepts light in the cone of observation 318. Filter 312 is an interference filter which is designed to pass only those wavelengths which lie in a narrow band, for example, those wavelengths centered around the "blue" wavelength $\lambda_1$ to multiplier phototube 311A. Filter 312 is supported at an angle with respect to the cone of observation 318 so as to reflect the light incident thereon which has not been passed to a second interference filter 313 supported in front of multiplier phototube 311C. Interference filter 313 is designed to pass only those wavelengths centered around a wavelength intermediate the wavelengths $\lambda_1$ and $\lambda_3$, for example, a "green" wavelength $\lambda_2$, to a multiplier phototube 311C. The light incident on filter 313 which is not passed thereby is reflected to a third interference filter 314 which is supported in front of multiplier phototube 311B and which is designed to pass only those wavelengths centered around the "red" wavelength $\lambda_3$ to multiplier phototube 311B.

The output signals from phototubes 311A, 311B, and 311C are supplied on lines 312A, 312B, and 312C to gates 335, 336, and 337, respectively. These signals comprise photoelectrons resulting from photons incident upon the corresponding multiplier phototube, in the band of wavelengths determined by the associated interference filter, and electrons resulting from the phototube's dark current, and noise.

A tungsten filament incandescent bulb has an emission characteristic very similar to that of a black body so that the light intensity at all wavelengths can be specified by measurement of intensity at two separate wavelengths (Planck's equation). For relatively small changes in the emission temperature of the bulb and over a limited range of wavelenghs, a linear approximation can be made to Planck's equation. Using such an approximation, the output signals on lines 326A, 326B are applied across a voltage divider in circuit 330 on whose taps the signals 331, 332, and 333 appear which represent the intensities at the desired wavelengths $\lambda_1$, $\lambda_2$, and $\lambda_3$. The gates 335, 336, and 337 may include circuitry similar to that illustrated in FIG. 3 in which the duty cycle of the respective multiplier phototube output is varied in response to the magnitude of the corresponding intensity signal on lines 331, 332, or 333.

The output from gates 335, 336, and 337 are supplied to a corresponding plurality of photon-detecting apparatuss 338, 339, and 340, which are identical in construction to that previously described for the embodiments in FIGS. 1, 4, and 6. Accordingly, the outputs from the photon-detecting apparatus 338, 339, and 340 comprise digital pulse trains, wherein each pulse represents either a photoelectron, or a thermally emitted "dark current" electron, and are supplied in parallel to a plurality of measurement and dark current compensation circuits 341, 342, and 343. Each of the circuits 341, 342, and 343 may be similar or identical in construction to the corresponding circuits previously described for the embodiments in FIGS. 1, 4, and 6. For example, this apparatus in FIG. 1 includes a portion of the circuit extending from the input of scale counter 46 to the output of subtractor 51.

As with the embodiment in FIG. 3, the dark current compensation in each of the circuits 341, 342, and 343 is varied in response to the corresponding reference intensity signal on lines 331, 332, and 333.

Each of the circuits 341, 342, and 343 therefore provides averaging of the input digital pulse train, scale adjustment, conversion into analog form, and compensation for dark current to obtain an output signal proportional to the desired extinction coefficient $b_{scat}$ at the desired center wavelength, that is $b_{scat}(\lambda_1)$, $b_{scat}(\lambda_2)$ and $b_{scat}(\lambda_3)$.

With reference to FIGS. 8–13, a multi-wavelength integrating nephelometer is illustrated which utilizes a continuously energized light source and photon-detecting apparatus similar to the embodiment illustrated in FIG. 7. A measurement electronics is also included which compensates for dark current, Rayleigh scatter, and "background" reflections by measuring ambient aerosol and clean purge air during separate time periods, and subtracting the values thus obtained in a manner similar to the embodiment illustrated in FIG. 6. However, this multiwavelength instrument is distinguished from those previously described in its capability for automatic recalibration to eliminate errors due to long-term drift during an extended period of unattended use. The instrument additionally provides for measurement of both the extinction coefficient $b_{scat}$, and the component of the extinction coefficient $b_{scat}$ which is due to back scatter only.

The measurement of the back scatter component $b_{scat}$ is desirable because such a component gives an indication of the effect of atmoshperic aerosol in reducing solar radiation that reaches the earth's surface. Light scattering through angles of 90° to 180°, which has been heretofore defined as comprising back scatter, is that which causes solar radiation to be reflected back into space, whereas light-scattering over angles of 0° to 90°, which is herein defined as forward scatter, changes the direction of solar radiation but still permits that radiation to reach the earth's surface.

Figure 8:
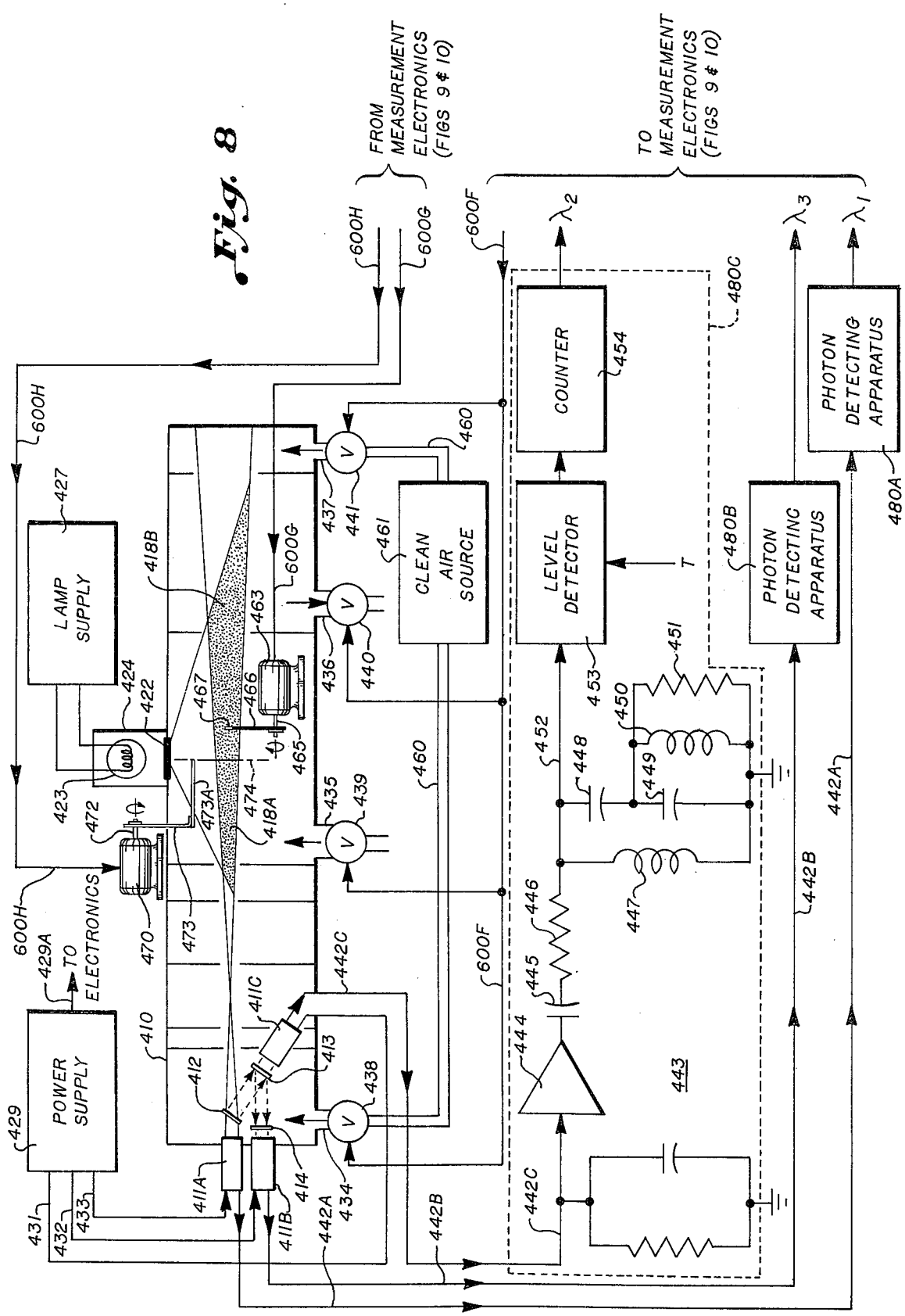
FIG. 8 is a schematic sectional view of a fourth embodiment of the improved integrating nephelometer, including a combined schematic and block diagram of its optical and a portion of its electronic systems and illustrating a multi-wavelength instrument which is self-calibrating and which is capable of measuring not only the extinction coefficient due to light scattering, but also the back scatter component of such extinction coefficient.

In FIG. 8, an integrating nephelometer optical system 410 includes a light source comprising a lamp 423 which is disposed in a housing 424. The RMS value of the voltage across lamp 423 is regulated by a lamp supply 427, which may comprise a conventional source of regulated supply voltage designed to be relatively stable over the time period of nephelometer operation between calibration cycles, as hereinafter described. No measurement of the lamp intensity is made, in contrast to the embodiments previously described.

An opal glass diffuser 422 is situated so as to conduct light from the lamp 423 to the central or sample section of the nephelometer 410. The optical center of the light beam produced by diffuser 422 is denoted by dashed line 474 in FIG. 8. As with the previous nephelometers, a cone of observation of that light beam is established by a plurality of spaced, apertured plates located within the nephelometer 410.

A plurality of multiplier phototubes 411A, 411B, and 411C are provided, with the multiplier phototubes 411A and 411B being situated in the forward end of the nephelometer 410, and multiplier phototube 411C being likewise located in the forward end but within the interior of nephelometer 410.

A beam splitter apparatus is provided for directing light from the cone of observation, shown in FIG. 8 as being divided into a forward scatter portion 418A and a back scatter portion 418B, to phototubes 411A, 411B, and 411C. A first filter 412 is supported, by means not illustrated, along the longitudinal axis of the nephelometer 410 in front of phototube 411A and intercepts light passing through the vertix of the cone of observation. Filter 412 is a dichroic interference filter which is designed to pass only those wavelengths which lie in a narrow band, for example, those wavelengths centered about the "blue" wavelength $\lambda_1$, to multiplier phototube 411A. Filter 412 is supported at an angle with respect to the axis of the cone of observation so as to reflect the light incident thereon which is not within its passband to a second dichroic interference filter 413 supported in front of multiplier phototube 411C. The filter 413 is designed to pass only those wavelengths centered around the "green" wavelength $\lambda_2$ to phototube 411C. The light incident on filter 413 which is not within its passband is reflected to a dye filter 414 which is supported in front of multiplier phototube 411B and which is designed to pass only those wavelengths centered around the "red" wavelength $\lambda_3$ to multiplier phototube 411B.

The arrangement and construction of multiplier phototubes 411A, 411B, and 411C, and the accompanying filters 412, 413, and 414, are similar to those previously described with respect to the multi-wavelength embodiment illustrated in FIG. 7.

The phototubes 411A, 411B, and 411C are energized by a power supply 429 which provides separate output voltages on lines 431, 432, and 433 to phototubes 411C, 411B, and 411A, respectively. Power supply 429 includes means, not illustrated, for independent adjustment of the output voltages on lines 431, 432 and 433 to allow adjustment of the gain of each associated phototube 411C, 411B, and 411A, respectively, to compensate for manufacturing variations among phototubes. In the preferred embodiment, a single power supply may be provided with its output connected to lines 431, 432 and 433 through separate variable resistors.

The output signals present on the leads 442A, 442B, and 442C from multiplier phototubes 411A, 411B, and 411C comprise pulses resulting from photoelectrons created by photons incident upon the multiplier phototube in the band of wavelengths determined by the corresponding filter, and from electrons created by dark current and noise.

These output signals are supplied to corresponding photon-detecting apparatus 480A, 480B, and 480C. Only apparatus 480C is illustrated in detail in FIG. 8, with elements 480A and 480B being identical in construction.

Each pulse is initially stretched by an R.C. circuit 443 connected from line 442C to reference potential. The "stretched" pulses on line 442C are inverted and amplified by an amplifier 444 whose output is coupled through a capacitor 445 and a series-connected resistor 446 to appear on a line 452. The output pulses on line 452 are modified by a pulse shaping network including an inductor 447 and series-connected capacitors 448, 449, which are both connected from line 452 to reference potential. A second inductor 450 and a resistor 451 are connected in parallel with capacitor 449. The pulse-shaping network functions to shape the sharply rising, slowly decaying pulses provided at the output of amplifier 444 into pulses having an amplitude which is related thereto and a width which is determined by the network. Accordingly, the pulse shaping network functions in a manner similar to the delay line clipper 44 previously described with respect to the embodiment illustrated in FIG. 1.

The level detector 453 is supplied with an input threshold signal T which is set at a level sufficient to allow the level detector 453 to provide an output pulse for each input pulse thereto which is a result of a photoelectron or "dark current" electron. However, level detector 453 will not provide an output pulse for the lower-magnitude pulses and signals resulting from noise.

Alternately, pulse shaping may be provided at the output of each of the multiplier phototubes, with subsequent amplification and level detection.

The output of level detector 453 is supplied to the input of a counter 454 which, in one embodiment, may be a divide by 4 counter. Counter 454 operates to reduce randomness of occurrence of the pulses comprising the output from level detector 453 to reduce possible error resulting from the inability of the measurement electronics, illustrated in FIGS. 9 and 10 and hereinafter described, to count all pulses detected. Therefore, counter 454 provides an averaging function similar to that of counter 46 previously described.

The output from the photon-detecting apparatus 480C, or the output of counter 454, appears on the line labeled $\lambda_2$ in FIG. 8. Similarly, the outputs from the photon-detecting apparatus 480B and 480A appear on the lines labeled $\lambda_3$ and $\lambda_1$, respectively, in FIG. 8. The lines $\lambda_1$, $\lambda_2$, and $\lambda_3$ are connected to the measurement electronics portion illustrated in FIGS. 9 and 10 and described hereinafter.

Figure 9:
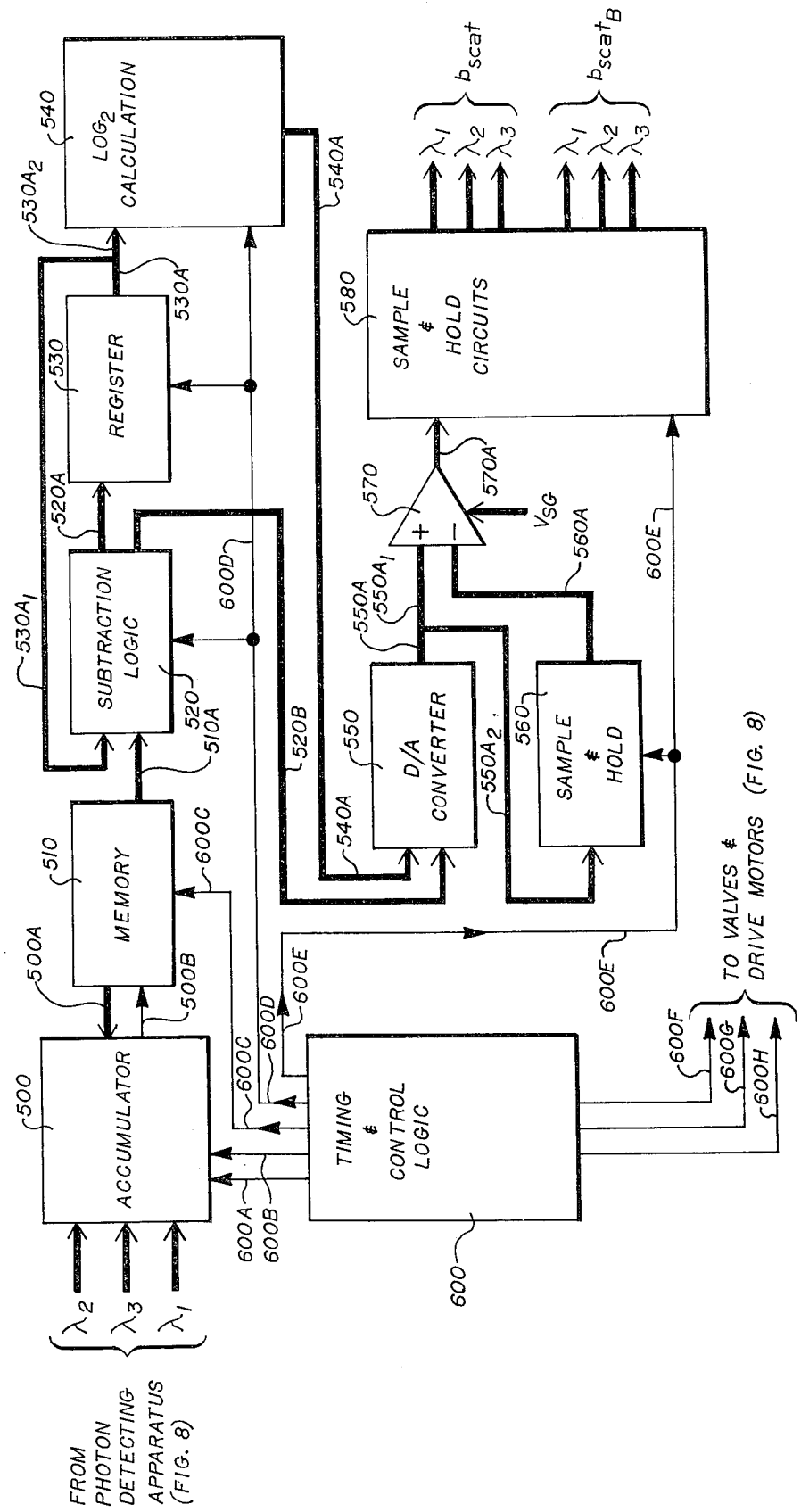
FIG. 9 is a block diagram illustrating a second portion of the electronics system of the fourth embodiment illustrated in FIG. 8.
Figure 10:
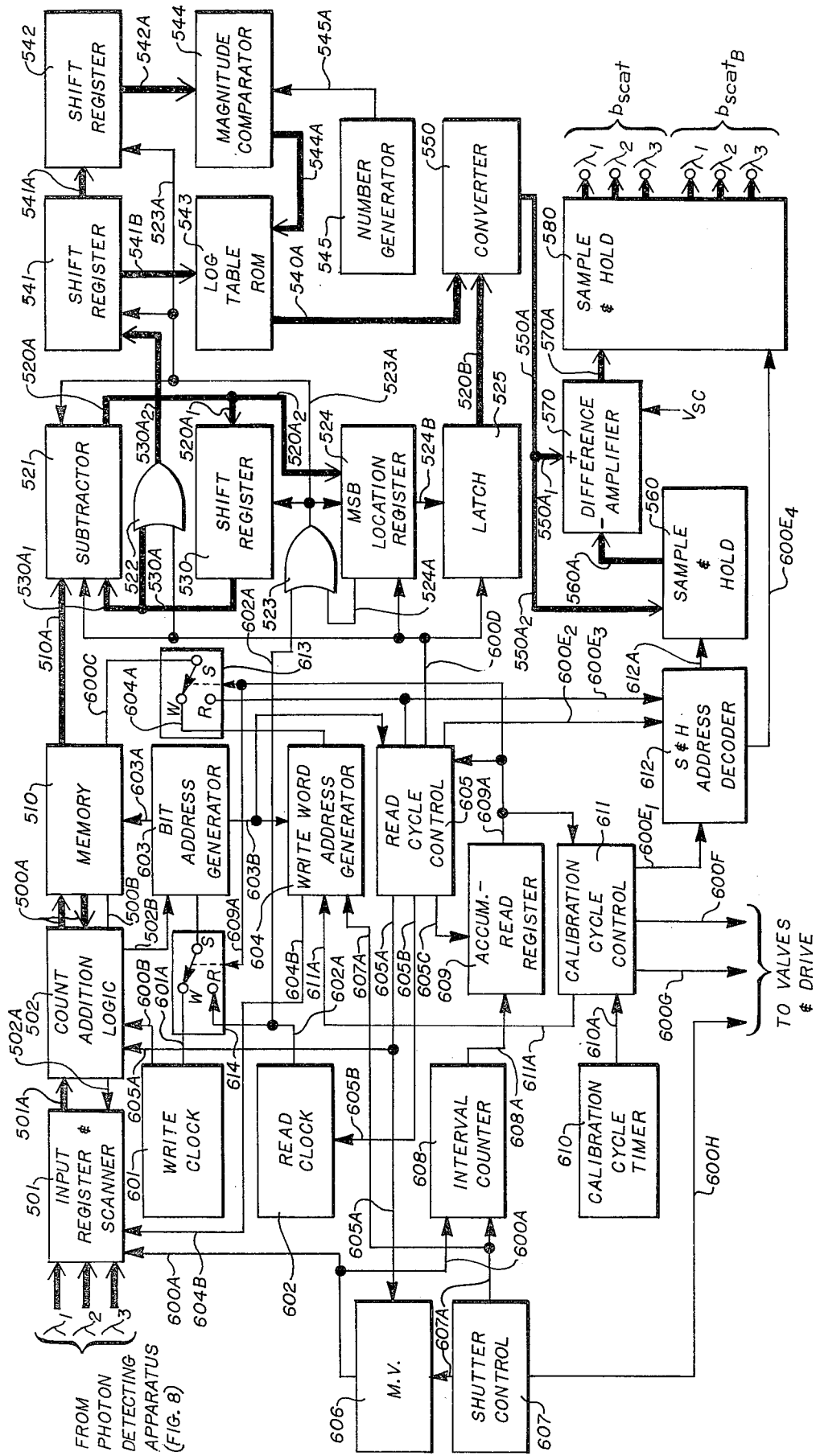
FIG. 10 is a more detailed block diagram of the electronics system illustrated in FIG. 9.

In order to measure the back scatter component of the extinction coefficient at the wavelengths $\lambda_1$, $\lambda_2$, and $\lambda_3$, a shutter 473 is included which is shown schematically in FIG. 8. The shutter 473 is attached to and rotatable with a shaft 472 of a two-position motor 470 and includes an opaque portion 473A which is located in one position in the vicinity of opal glass diffuser 422. A line 600H couples the motor 470 to the measurement electronics portion of the nephelometer (FIGS. 9 and 10). When an actuating signal is provided on line 600H, the motor 470 rotates the shaft 472 to place the shutter 473 into the position illustrated in FIG. 8, wherein the opaque portion 473A blocks a portion of the light beam emitted through opal glass diffuser 422 which extends from the centerline 474 in the direction of the multiplier phototubes 411A, 411B, and 411C. This portion of the light beam has been previously denoted 418A. Accordingly, forward scatter, or that over scattering angles of 0° to 90°, is blocked. However, a portion of the light beam passing through opan glass diffuser 422 which extends from center line 474 in a direction away from the multiplier phototubes 411A, 411B, and 411C is not blocked. This portion has been previously denoted 418B. Accordingly, back scatter, or that over scattering angles of 90° – 180°, is not blocked.

When the actuating signal on line 600H is removed, motor 470 rotates shaft 472 in the direction of the arrow in FIG. 8 so that shutter 473 assumes a position, not illustrated, in which the opaque portion 473A does not interfere with the beam from opal glass diffuser 422. In this case, the entire beam including portions 418A and 418B illuminates the aerosol sample.

In order to correct for Rayleigh scatter, "dark current" and "background" reflections, a source of clean purge air 461 is included which is connected by a conduit 460 to valves 438, 441 located in purge air inlets 434, 437 located at the ends of the nephelometer 410. Also provided are valves 439 and 440 located, respectively, in the inlet 435 and outlet 436 which are located adjacent the central or sample section of the nephelometer 410. The source of ambient air to be measured is introduced through valve 439 and inlet 435 and all air is exhausted through outlet 436 and valve 440.

Valves 438, 439, 440, and 441 are actuated under control of signals symbolized as appearing on a line 600F in FIG. 8. These signals are provided by the measurement electronics (FIGS. 9 and 10) and function to cause either ambient air or clean purge air to be circulated through the nephelometer 410.

A calibration apparatus is provided including a calibration scatterer 467 which is disposed on the end of a support 466. Support 466 is attached to and rotatable with a shaft 465 of a two-position motor 463. A line 600G couples the motor 463 to the measurement electronics portion (FIGS. 9 and 10). When an actuating signal is provided on line 600G, motor 463 rotates shaft 465 to place the calibration scatterer 467 and support 466 in the position illustrated in FIG. 8 where calibration scatterer 467 is in the cone of observation. In a working model, the support 466 comprised a fine wire attached to and looped around the shaft 467 which was painted black. The tip of the wire was painted with kodak white reflectance paint including a barium sulfate pigment to form the calibration scatterer 467.

When the actuating signal on line 600G is removed, motor 463 rotates shaft 465 to move the calibration scatterer 467 out of the cone of observation.

A truly white object over the wavelengths of interest, such as one coated or painted with the kodak paint mentioned above, is one which produces a known value of the extinction coefficient $b_{scat}$. Further, it has been ascertained that the value of $b_{scat}$ so obtained from an object coated or painted with the kodak paint is not dependent on wavelength, that is, the exponent $\alpha$ previously discussed is equal to zero. Accordingly, the use of the calibration scatterer 467 allows compensation for the different sensitivity of each wavelength channel in the nephelometer embodiment of FIG. 8, caused by the different emission characteristics of a tungsten filament incandescent bulb previously described at different wavelengths, by the different transmission characteristics and band widths of the filters 412 and 413, and by the different sensitivities of the multiplier phototubes 411A, 411B and 411C. In addition, when the calibration apparatus is operated periodically as hereinafter described, the apparatus allows compensation for long term drift in the instrument due to the above-identified factors resulting in different wavelength sensitivity of each measurement channel.

The apparatus to be described with respect to FIG. 9 uses a technique of data handling in which both calibration counts for $\lambda_1$, $\lambda_2$, and $\lambda_3$, for total scatter, and measurement counts for $\lambda_1$, $\lambda_2$, and $\lambda_3$, for total scatter and back scatter, are compensated for Rayleigh scatter, "dark current" and "background" reflections by subtraction of counts obtained when clean purge air is present in the nephelometer to obtain "compensated" calibration and measurement counts.

The desired extinction coefficients are then obtained by dividing the compensated total scatter and back scatter measurement counts for $\lambda_1$, $\lambda_2$, and $\lambda_3$ by the corresponding compensated calibration counts for $\lambda_1$, $\lambda_2$, and $\lambda_3$ to obtain normalized measurement counts. This division may be accomplished by obtaining the $\log_2$ of the compensated measurement counts and subtracting the $\log_2$ of the corresponding compensated calibration counts.

In the measurement electronics portion illustrated in FIG. 9, in which data transmission signal paths are signified by dark lines and timing and control signal paths are signified by light lines, the pulses on lines $\lambda_1$, $\lambda_2$, and $\lambda_3$ are supplied to an accumulator 500 which may comprise a plurality of registers, one being provided for each of the lines $\lambda_1$, $\lambda_2$, and $\lambda_3$. Each of the registers in accumulator 500 is arranged to accumulate the pulses on its input line for the duration of an enabling signal on line 600A, which signal is provided by a timing and control logic 600. The contents of each register are scanned by a multiplexer, also not illustrated but within accumulator 500, under control of a select signal on a line 600B from timing and control logic 600, and gated to update a digital memory 510 via a plurality of data lines 500A and a control line 500B.

The digital memory 510 may comprise a digital memory having a plurality of storage locations which are addressable under control of an address signal on line 600C from timing and control logic 600. For convenience, the storage locations may be grouped into words. In the embodiment illustrated, the storage locations are grouped into fifteen words of 20 storage locations (bits) apiece, a word being assigned for each of the wavelengths $\lambda_1$, $\lambda_2$, and $\lambda_3$ to accumulated pulses (counts) for a) total scatter for an ambient air sample (hereinafter $TS_{ambient}$); b) back scatter for an ambient air sample (hereinafter $BS_{ambient}$); c) total scatter for a clean air sample (hereinafter $TS_{clean\ air}$); d) back scatter for a clean air sample (hereinafter $BS_{clean\ air}$); and e) total scatter of a calibration scatterer for a clean air sample (hereinafter $TS_{cal}$).

Under control of the address signal on line 600C and a corresponding select signal on line 600B, accumulator 500 and memory 510 operate to continuously update the words in memory 510 throughout successive accumulating intervals defined by the enabling signal on line 600A. At the end of each accumulating interval, the counts in each of the words in memory 510 corresponds to the accumulated counts for that word during the accumulating interval.

Timing and control logic 600 also provides signals on line 600F, 600G, and 600H to the valves and drive motors in FIG. 8 previously described.

The portions of the embodiment in FIG. 9 establish, under control of timing and control logic 600, an accumulating cycle which is composed of a predetermined number of accumulating intervals. For example, each accumulating cycle may be of 32 seconds duration including 16 accumulating intervals, each of slightly less than 2 seconds.

Throughout each accumulating cycle, a signal is provided on line 600F to open valves 439 and 440 and close valves 438 and 441 so that ambient air is circulated through the nephelometer 410.

Shortly after the beginning of the first accumulating interval in the accumulating cycle, timing and control logic 600 removes the actuating signal from line 600H to cause the opaque portion 473A to be moved out of interference with the light beam emanating from opal glass diffuser 422. Shortly after this time, timing and control logic provides an enabling signal on line 600A so that the pulses on lines $\lambda_1$, $\lambda_2$, and $\lambda_3$ are accumulated. During the first accumulating interval, appropriate address and select signals are provided on lines 600B and 600C so that the accumulated counts update the counts stored in memory 510 for the words $TS_{ambient}$ $\lambda_1$, $TS_{ambient}$ $\lambda_2$, and $TS_{ambient}$ $\lambda_3$. At the end of the first accumulating interval, the timing and control logic 600 removes the enabling signal 600A. Also, timing and control logic 600 provides a signal on line 600H to cause the opaque portion 473A to be moved into interference with the light beam emanating from opal glass diffuser 422.

During a succeeding second accumulating interval, timing and control logic 600 provides an enabling signal on line 600A and appropriate address and select signals on lines 600C, 600B to cause the accumulated counts to update the counts stored in memory 510 for the words $BS_{ambient}$ $\lambda_1$, $BS_{ambient}$ $\lambda_2$, and $BS_{ambient}$ 80 $_3$.

Throughout the remainder of the accumulating cycle, the measurement and updating of $TS_{ambient}$ and $BS_{ambient}$ for $\lambda_1$, $\lambda_2$, and $\lambda_3$ alternates in successive accumulating intervals. At the end of the accumulating cycle, the counts stored in memory 510 represent counts for the words $TS_{ambient}$, $BS_{ambient}$ for the wavelengths $\lambda_1$, $\lambda_2$, and $\lambda_3$ accumulated during one-half of the accumulating cycle, or approximately 16 seconds.

Also stored in memory 510 are counts for the words $TS_{clean\ air}$, $TS_{cal}$, $BS_{clean\ air}$ and $BS_{cal}$, for $\lambda_1$, $\lambda_2$, and $\lambda_3$ which are obtained during a calibration cycle to be described hereinafter.

Timing and control logic 600 terminates the accumulating cycle and initiates a read cycle by inhibiting the enabling signal on line 600A and by providing readout address signals to the memory 510 on line 600C. A serial data line 510A connects the output stages of memory 510 to a subtraction logic 520 whose first output is denoted 520A and is connected to a register 530. A second output is denoted 520B and is connected to a first input of a D/A converter 550. The output of register 530, denoted 530A, is split into two parts, comprising a line 530A$_2$ which is connected to a log$_2$ calculation circuit 540, and a line 530A$_1$ which is connected to a second input of subtraction logic 520. The output of log$_2$ calculation circuit 540, denoted 540A, is connected to a second input of D/A converter 550 whose output 550A is split into a part 550A$_1$ connected to a first input of a difference amplifier 570 and a second part 550A$_2$ connected to the input of a sample and hold circuit 560. An output 560A from sample and hold circuit 560 is connected to a second input of difference amplifier 570, which also has as an input a scaling voltage $V_{sc}$. The output of difference amplifier 570, denoted 570A, is connected to the inputs of a plurality of sample and hold circuits 580.

For the embodiment being described, there are six sample and hold amplifiers in circuits 580 for storing analog signals corresponding to the extinction coefficient $b_{scat}$, for $\lambda_1$, $\lambda_2$, and $\lambda_3$, and the back scatter component $b_{scat}$, for $\lambda_1$, $\lambda_2$, and $\lambda_3$.

Under control of the timing and control logic 600, by virtue of signals provided on lines 600B, 600C, 600D, and 600E, the read cycle proceeds in the following manner.

In a first read interval, timing and control logic 600 provides a readout address signal on line 600C and a control signal on line 600D to transfer the words $TS_{clean\ air}$ in memory 510 serially through the subtraction logic 520 into register 530. In a second read interval, the word $TS_{cal}$ is similarly shifted into subtraction logic 520, as is the word $TS_{clean\ air}$ from register 530. Subtraction logic 520 is enabled by an appropriate control signal on line 600D to subtract $TS_{clean\ air}$ from $TS_{cal}$ and to shift the result ($TS_{cal}$ - $TS_{clean\ air}$) into register 530. At the same time, the location of the most significant bit of the result is retained in subtraction logic 520.

In the embodiment being discussed, the log$_2$ calculation is performed in a third read interval by considering the number stored in register 530 to be in the form of $2^n(A)$, where $n$ is an integer, and $1 \le A < 2$. The log$_2$ of such a number equals $n + \log_2(A)$. With binary numbers as used in the present embodiment, $n$ equals the number of bits between the $2^0$ position in the number and the most significant bit of that number. As has been described, the determination of $n$ is accomplished within subtraction logic 520 which provides a corresponding output on line 520B to D/A converter 550. The log$_2$ calculation circuit 540 acts only on the component A of the number in register 530 and presents an output digital signal representing log$_2(A)$ on line 540A to D/A converter 550 under control of appropriate control signals for timing and control logic 600 on line 600D. D/A converter 500 provides the sum ($n + \log_2(A)$) and converts the sum to an analog signal appearing on line 550A.

At the termination of the third read interval, the read cycle is inhibited for a predetermined period of time under the control of control signals on lines 600D, 600E from timing and control logic 600 to allow the analog signal on line 550A (550A$_2$) to be stored in sample and hold circuit 560. The signal stored represents the compensated calibration count for $\lambda_1$.

In a next group of three read intervals, the words TS$_{clean\ air}$ and TS$_{ambient}$, are obtained from memeory 510. In a manner identical to that described for the first group of three read intervals, the log$_2$ of (TS$_{ambient}$ - TS$_{clean\ air}$) is obtained and appears as an analog signal on the output 550A of D/A converter 550. At the termination of the sixth read interval, the read cycle is inhibited for a predetermined period of time under control of control signals on lines 600D and 600B from timing and control logic 600 to allow the difference amplifier 570 to subtract log$_2$ (TS$_{cal}$ - TS$_{clean\ air}$) from log$_2$ (TS$_{ambient}$ - TS$_{clean\ air}$) and add a constant $V_{sc}$ for scaling purposes. The resulting extinction coefficient $b_{scat}(\lambda_1)$ is immediately stored in one of the sample and hold circuits 580.

During a next group of three read intervals, the words BS$_{clean\ air}$ and BS$_{ambient}$ are obtained from memory 510. In a manner identical to that previously described, the log$_2$ of (BS$_{ambient}$ - BS$_{clean\ air}$) is obtained and appears as an analog signal on the output 550A of D/A converter 550. At the termination of the ninth read interval, the read cycle is inhibited for a predetermined period of time under control of control signals on lines 600D and 600E from timing and control logic 600 to allow the difference amplifier 570 to subtract log$_2$ (TS$_{cal}$ - TS$_{clean\ air}$) from log$_2$ (BS$_{ambient}$ - BS$_{clean\ air}$) and add a constant $V_{sc}$ for scaling purposes.

It should be noted that the back scatter measurement counts are thereby normalized by division by the same total scatter calibration counts that are used to normalize the total scatter measurement counts.

The result, representing the desired back scatter component of the extinction coefficient, $b_{scat}$ ($\lambda_1$) is immediately stored in one of the corresponding sample and hold circuit 580.

The sequence of nine read intervals which has just been described is then repeated for the accumulated counts for the wavelengths $\lambda_2$ and $\lambda_3$. At the end, therefore, of 27 read intervals, sample and hold amplifiers 580 contain the extinction coefficient $b_{scat}$, and the back scatter component of that extinction coefficient, $b_{scat}$, for the wavelengths $\lambda_1$, $\lambda_2$, and $\lambda_3$, which has been calculated from the data acquired during the preceding accumulating cycle. Because of the speed with which the largely digital measurement electronics may operate, the read cycle may take less than 0.2 seconds to complete.

Thereafter, timing and control logic begins another accumulating cycle by terminating the control signals on lines 600, 600D, and 600E and producing enabling, select, and address signals on lines 600A, 600B, and 600C, and actuating signals on line 600G, all as previously described.

During each accumulating cycle, the sample and hold circuits 560, 580 retain the signals stored therein during the preceding read cycle.

When the instrument is first turned on, and every predetermined period thereafter, e.g., every 15 minutes, the timing and control logic 600 operates to define a calibration cycle as follows.

At the start of a calibration cycle, timing and control logic 600 provides control signals on line 600F to close valve 439, thereby shutting off the source of ambient air, and to open valves 438, 440, and 441. Thereafter, clean air from the clean air source 461 is circulated throughout the instrument. After a first period of time sufficiently long to allow ambient air to be purged from the nephelometer, for example, equal in duration to that of one accumulating cycle and one read cycle, an enabling signal is provided on line 600A to accumulator 500 to begin a first calibration accumulating cycle. During this cycle, the opaque portion 473A is alternately moved in and out of interference with the light beam emanating from opal glass diffuser 422 on successive accumulating intervals to allow updating in memory 510 of the words TS$_{clean\ air}$, and BS$_{clean\ air}$ for wavelengths $\lambda_1$, $\lambda_2$, and $\lambda_3$. The operation of the measurement electronics during this calibration accumulating cycle is otherwise identical to that previously described for the measurement accumulating cycles.

Timing and control logic 600 then starts a second calibration accumulating cycle by providing an actuating signal on line 600G to cause the calibration scatter 467 to be moved into the cone of observation. Thereafter, enabling, select, addressing, and control signals are provided on lines 600A, 600B, 600C, and 600H to allow updating in memory 510 of the words TS$_{cal}$ for wavelengths $\lambda_1$, $\lambda_2$, and $\lambda_3$.

At the end of the second calibration accumulating cycle, timing and control logic 600 inhibits the enabling signal on line 600A and terminates the actuating signal on line 600G, returning the calibration scatter 467 to its position out of the cone of observation. At the same time, the control signals on line 600F are also changed to close valves 438 and 441, and open valve 439, thereby introducing ambient air once again into the nephelometer. After a second period of time sufficient to purge the nephelometer of clean air, for example equal to that of one accumulating cycle and one read cycle, enabling signals are again provided on line 600A and the next measurement accumulating cycle is begun.

During the first period of time described above in which the nephelometer is purged of ambient air by the introduction of clean air, a control signal is provided on line 600E to inhibit the operation of sample and hold circuits 560 and 580. At the termination of the first calibration accumulating cycle, a first calibration read cycle occurs by operation of the timing and control logic 600 as previously described. During this first calibration read cycle, the calculations necessary to obtain the $b_{scat}$ and $b_{scat}$ values are carried out using the newly acquired values for the words TS$_{clean\ air}$ and BS$_{clean\ air}$ for the wavelengths $\lambda_1$, $\lambda_2$, and $\lambda_3$, and the previously-acquired values for the words TS$_{ambient}$, BS$_{ambient}$ and TS$_{cal}$ for the wavelengths $\lambda_1$, $\lambda_2$, and $\lambda_3$. The results of these calculations are stored in sample and hold circuits 580.

At the termination of the second calibration accumulating cycle, a second calibration read cycle is initiated by timing and control logic 600. During the second calibration read cycle, new values for $b_{scat}$ and $b_{scat}$ are calculated, using the newly acquired values for the words TS$_{cal}$, TS$_{clean\ air}$, and BS$_{clean\ air}$, for the wavelengths $\lambda_1$, $\lambda_2$, and $\lambda_3$, and the previously-acquired values for the words TS$_{ambient}$ and BS$_{ambient}$, for the wavelengths $\lambda_1$, $\lambda_2$, and $\lambda_3$. The results of these calculations are then stored in the sample and hold circuits 580.

During the second period of time, a control signal is provided on line 600E to inhibit the operation of sample and hold circuits 560 and 580.

Inhibiting of sample and hold circuits 560 and 580 during the first and second periods of time previously described is required in order to avoid obtaining erroneous values for $b_{scat}$ and $b_{scat}$ during a time when the nephelometer is filled with a mixture of ambient and clean air.

The block diagram of FIG. 10 illustrates in more detail the embodiment of the invention illustrated in FIG. 9, and corresponding elements have been given corresponding numerals. Reference should also be made to the timing diagrams in FIGS. 11–13.

The output pulses from the plurality of photon-detecting apparatus in FIG. 8, which appear on lines $\lambda_1$, $\lambda_2$, and $\lambda_3$, are supplied to an input register and scanner 501 which comprises three single-bit digital registers, one for each of the lines $\lambda_1$, $\lambda_2$, and $\lambda_3$, and a multiplexer or scanner for connecting each of the registers in turn to a count addition logic 502 via data line 501A. An input signal on a line 502A from count addition logic 52 resets each of the registers within the circuit 501 as hereinafter described.

During each accumulating cycle, a shutter control circuit 607 provides alternating logic 1 and logic 0 output pulses on line 600H (FIG. 11) to define alternating back scatter and total scatter accumulating intervals. These pulses cause the opaque portion 473A to be moved in and out of interference with the light emanating from opal glass diffuser 422. In addition, shutter 607 provides alternating logic 1 and logic 0 pulses on a line 607A, whose changes in logic state are delayed from the changes in logic state of the pulses provided on line 600H by the amount of time necessary to allow the opaque portion 473A to complete its movement between positions. The pulses on line 607A are applied to a multi-vibrator 606 which provides, for every change in logic state of the pulses on line 607A, an enabling output pulse on line 600A for a predetermined time period less than the duration of each pulse on line 607A. The enabling output pulses on line 600A define the accumulating intervals and enable the three registers within input register and scanner 501 for their duration. The early termination of each enabling pulse allows the opaque portion 473A to begin to move between its alternate positions.

The pulses on line 607A are also supplied to an interval counter 608 and a write word address generator 604. The interval counter 608 also has supplied thereto the enabling pulses on line 600A. On each concurrence of a logic change in the pulses on line 600A from a logic 1 to a logic 0 and a logic 1 on line 607A, interval counter 608 is stepped by one. When the count within interval counter 608 reaches a predetermined number, such as 16 in the present embodiment, an output is provided thereby on line 608A to an accumulate-read register 609 to terminate the accumulating cycle as hereinafter described.

The logic state of the pulses on line 607A also sets write word address generator 604 to select a word address in memory 510 for back scatter or total scatter counts. In response to the pulses on line 607A and on a line 603A from a bit address generator 603 hereinafter described, write word address generator 604 produces an address signal on a line 604A, which address signal specifies the location in memory 510 of the word into which data from the input register and scanner 501 is to be entered. This addresss signal passes to a multiplexer 613 symbolized in FIG. 10 as a switch having a movable contact S and stationary contacts W and R.

When the signal on line 609A is a logic 0, which is the normal state of accumulate-read register 609 during the accumulating cycle, multiplexer 613 operates to pass the address signal on line 604A through symbolized contacts W and S to line 600C which is coupled to memory 510. At the same time, write word address generator 604 supplies a select signal on a line 604B to the input register and scanner 501. The select signal on line 604B denotes which of the three registers is to be coupled by the multiplexer in input register and scanner 501 to count addition logic 502 and cause the contents of the selected input register to be transferred via data lines 501A to a carry register, not illustrated, within count addition logic 502 which produces a reset signal on a line 502A to clear the selected input register within input register and scanner 501.

During transfer, the storage locations assigned to the word being updated are addressed by the address signal on line 600C. The bit address generator provides a bit address signal on line 603A to memory 510 which addresses the bits of a word in group of bits. In its initial rest state, the bit address signal on line 603A causes the four least significant bits of the stored word to be transferred via data lines 500A to count addition logic 502, wherein they summed summemd with the count that has been previously transferred from input register and scanner 501. The sum is then written in the same storage locations by transfer via lines 500A under control of a write command signal on a line 500B. If the sum includes a carry beyond the four least significant bits, the carry bit is stored in the carry register within count addition logic 502 and a carry output signal is provided on a line 502B to bit address generator 603.

These transfer, addition, and carry operations are carried out in a conventional manner at a rate determined by clock pulses from a write clock 601. The write clock pulses are provided to count addition logic 502 on a line 602B, and are provided to bit address generator 603 on a line 601A, as coupled through a multiplexer 614 symbolized in FIG. 10 as a switch having a movable contact S and stationary contacts W and R. When the signal on line 609A is a logic 0, multiplexer 614 operates to pass the write clock pulses on line 601A through symbolized contacts W and S to bit address generator 603.

If a carry output signal appears on line 502B, bit address generator provides a bit address signal on line 603A which causes the four next most significant bits of the stored word to be transferred on data lines 500A to count addition logic 502. The bit within the carry register is then summed with the data just transferred from memory 510 and the sum is written into the same storage locations by transfer via lines 500A under control of a write command signal on line 500B. If the sum also includes a carry, the carry bit is stored in the carry register and a carry output signal is provided on line 502B to bit address generator 603. If the carry output signal is not provided, bit address generator 603 resets to its initial state and provides an output signal on line 603B to step write word address generator 504 to its next position. The updating process just described is then repeated for the data in the next register within input register and scanner 501. In turn, write word address generator 604 provides appropriate outputs on lines 604A and 604B.

As so far described, the circuitry in FIG. 10 allows simultaneous accumulation of counts for the wavelengths $\lambda_1$, $\lambda_2$, and $\lambda_3$ during the accumulating cycle, and concurrent transfer of these accumulated counts into appropriate storage locations in memory 510 at a rate which is asynchronous with the rate of occurrence of accumulating intervals during the accumulating cycle.

At the end of sixteen accumulating intervals, interval counter 608 provides an output signal on line 608A which sets accumulate-read register 609 to a state wherein a logic 1 output signal is provided on its output line 609A. Thus logic 1 output signal is supplied to a calibration cycle control 611, for purpose hereinafter described, and to read cycle control 605. Additionally, the logic 1 output signal on line 609A is supplied to multiplexers 613 and 614 to cause the symbolized switches therein to make contact between symbolized contacts R and S therein. Accumulate-read register 609 remains in the state wherein its output signal is a logic 1 until reset by a signal on line 605C from read cycle control 605, as hereinafter described.

Figures 11, 12:
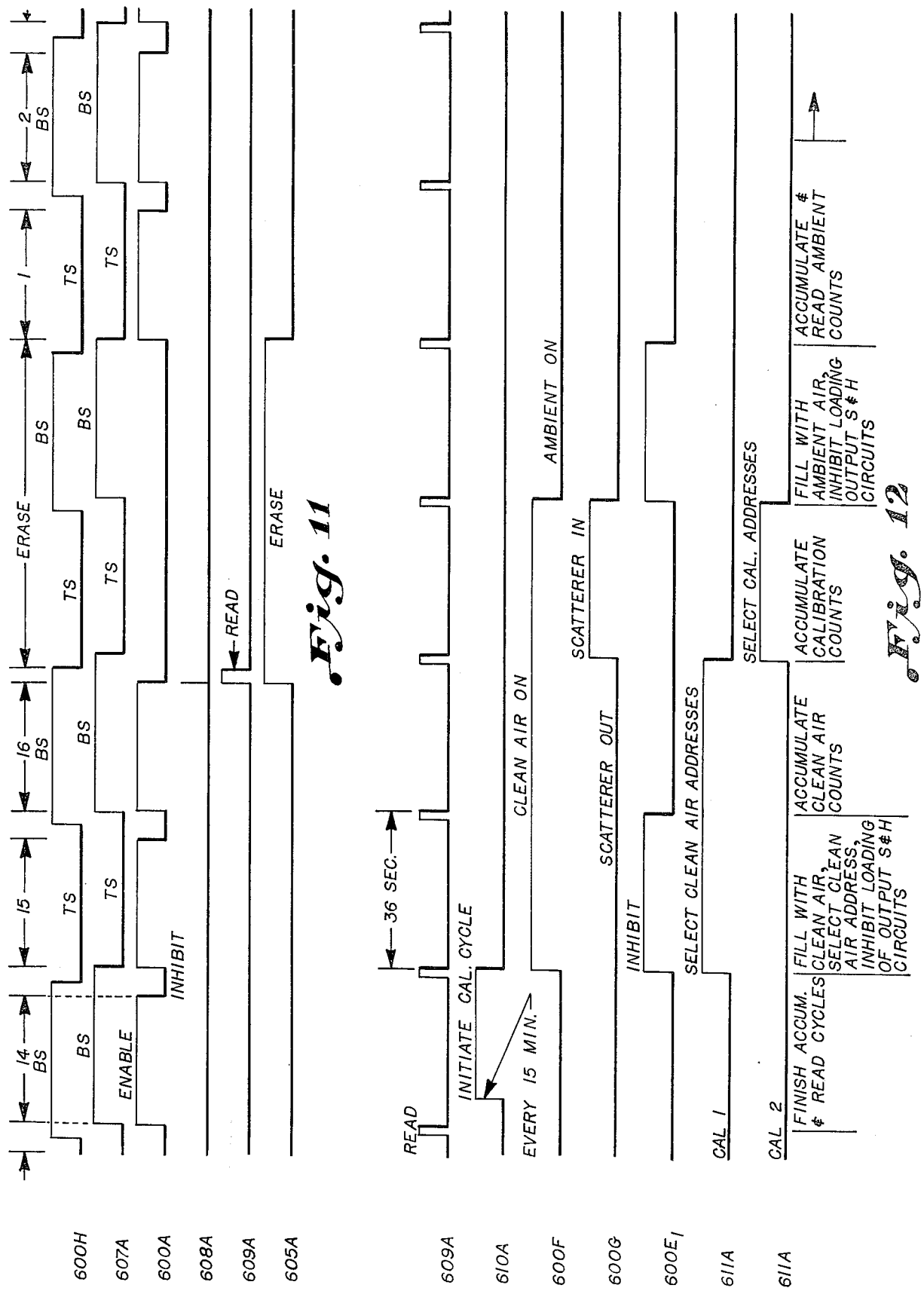

Read cycle control 605 provides an output signal on line 605A in response to the logic 1 output signal on line 609A which is supplied to inhibit the operation of multivibrator 606 for the duration of the read cycle and for one cycle of operation of the shutter control 607 thereafter which cycle may be termed an erase cycle (FIG. 11). The output signal on line 605A is also supplied to a gate, not illustrated, within count addition logic 502 which inhibits the contents of the three registers in input register and scanner 501 from being transferred to count addition logic 502. Accordingly, the contents of these registers appear to be zero for the duration of the signal on line 605A.

The erase cycle thereafter proceeds as a normal accumulating cycle would proceed. Accordingly, the data stored in the storage locations for the words $TS_{ambient}$ and $BS_{ambient}$ is erased effectively during the erase cycle, contents of these storage locations are replaced with zeroes through the updating process previously described.

The operation of multiplexer 614 at the start of the read cycle causes an output 602A of a read clock 602 to be coupled to the bit address generator 603 through symbolized contacts R and S. The read clock input steps the bit address generator 603 to provide bit address signals to memory 510 on line 603A to cause the bits of a word being addressed by an address signal on line 600C to be transferred in a serial fashion, least significant bit first, to output line 510A. Address signals are provided by an output of read cycle control 605 apppearing on line 600E₃, as coupled through multiplexer 613 (symbolized contacts R and S) and input line 600C.

The data appearing on lines 510A for a given wavelength group (e.g. $\lambda_1$) is seen in FIG. 13. At the time that the most significant bit of any word is addressed by bit address generator 603, an output pulse is provided thereby on line 603B to read cycle control 605 to cause read cycle control 605 to provide an address signal on line 600E₃ for the next word to be read.

Read cycle control 605 also provides a set of control signals (CONTROL 1 and CONTROL 2) on line 600D to a latch 525, a MSB location register 524, a gate 522, and a subtractor 521 to define the read intervals. When both CONTROL 1 and CONTROL 2 are a logic 0, subtractor 521 operates to pass the data on input lines 510A to its output lines 502A and into shift register 530 via line 520A₁.

During the first read interval the word $TS_{clean\ air}$ is transferred through subtractor 521 and into shift register 530. At the conclusion of the first read interval, the output pulse on line 603B from bit address generator 603 steps read cycle control 605 so that the CONTROL 1 signal shifts to a logic 1. The memory 510 is then addressed by read cycle control 605 to serially read out the word $TS_{cal}$. For the remainder of the second read interval, subtractor 521 has shifted therein $TS_{cal}$ on line 510A and $TS_{clean\ air}$ on line 530A₁ and provides the subtraction $TS_{cal} - TS_{clean\ air}$ on line 520A.

The shifting, transfer, and subtracting operations previously described are accomplished by gating the read clock signal appearing on line 602A through a gate 523, which is normally enabled, and therefore to shift register 530 and subtractor 521 on a line 523A.

During the second read interval, the logic 1 CONTROL 1 signal on line 600D inhibits a gate 552 so that logic 0 pulses are provided on its output line 530A₂. While $TS_{clean\ air}$ is being shifted out of shift register 530 on line 530A, $TS_{cal} - TS_{clean\ air}$ is being shifted into shift register 530 on line 520A₁.

$TS_{cal} - TS_{clean\ air}$ is also supplied to a MSB location register 524 on a line 520A₂. MSB location register 524 comprises a presettable down counter stepped by the gated read clock signal on line 523A. In the case of a 20 bit word, the MSB location register 524 is preset to a count of 19 whenever a logic 1 data bit from subtractor 521 appears at the input to shift register 530. When a logic 0 appears at the input to shift register 530, the MSB location register 524 steps down a count of 1 at the concurrence of a corresponding gated read clock pulse on line 523A. Accordingly, at the termination of the second read interval, the most significant bit (MSB) of $TS_{cal} - TS_{clean\ air}$ is present in the first or input stage of shift register 530 (assuming that data is shifted with the least significant bit (LSB) being read first). At this time, the count remaining in MSB location register 524 corresponds to the location of the most significant logic 1 bit of the word stored in shift register 530 and is supplied to latch 525 on line 524B.

At the occurrence of the next output pulse on line 603B from bit address generator 603, the second read interval is terminated and the third read interval is initiated. The output pulse on line 603B steps read cycle control 605 so that a logic 0 CONTROL 1 signal and a logic 1 CONTROL 2 signal are presented on line 600D. Subtractor 521 is thereby enabled to produce a continuous logic 0 output on line 520A. The logic 1 CONTROL 2 signal on line 600D causes latches 525 to store the count remaining in MSB location register 524 which is supplied on line 524B. This data, which comprises the location of the most significant logic 1 bit for the word stored in shift register 530 ($TS_{cal} - TS_{clean\ air}$) is conducted to D-to-A converter 550 by lead 520B and appears at the five most significant bit positions in D-to-A converter 550. The logic 0 CONTROL 1 signal on line 600D enables gate 522 so that the contents of shift register 530, or $TS_{cal} - TS_{clean\ air}$, appear on line 530A₂ and are shifted into shift registers 541 and 542 which form part of the $\log_2$ calculation circuit 540. Read cycle control 605 supplies an address signal on line 600E₃ which instructs sample and hold address decoder 612 to select sample and hold circuit 560 for loading.

The logic 0 ouput supplied on line 520A (520A₂) causes the MSB location register 524 to count down to zero under control of the gated read clock pulses on line 523A. When MSB location register 524 counts to zero, an output signal is provided on line 524A which opens gate 523 to inhibit the gated read clock signal on 523A (FIG. 13).

The termination of the gated read clock signal also terminates the shifting of data from gate 522 into shift registers 541 and 542 and terminates the counting of MSB location register 524. At this time, the most significant bit in the words $TS_{cal}$ - $TS_{clean\ air}$ is present on lead 530A ($530A_2$). Also, shift register 541 and 542 contain the bits in positions 2 through 9 of the word $TS_{cal}$ - $TS_{clean\ air}$.

As previously discussed, the $\log_2$ of a number $2^n(A) = n + \log_2(A)$, where $1 \leq A < 2$. Now the number N comprises the location of the most significant bit which is stored in latch 525 and present on lead 520B to D-to-A converter 550. The number stored in shift registers 541 and 542 comprises the quantity A - 1, since the most significant bit remains in shift register 530.

A log table Rom 543 is provided which comprises, in the embodiment being discussed, a 32 word read-only memory which has been programmed with 16 values of $\log_2(A)$, $1 \leq A \leq 1\ 15/16$. The data contained in shift register 541 comprises bits 2 through 5 of the number A and is conducted to the log table Rom 543 by four address lines in lead 541B. Accordingly, log table Rom 543 is enabled to provide an output signal on line 540A which represents an approximation to $\log_2(A)$. The signal appearing on line 540A is conducted to D-to-A converter 550 and is converted into a corresponding analog singal A on output 550A.

In order to improve the resolution of the $\log_2$ calculation, a magnitude comparator 544 and a number generator 545 are provided to perform, in accordance with the least significant bits in positions 6 through 9 stored in shift register 542, a linear interpolation between the 16 values of $\log_2(A)$ previously described which are stored in log table Rom 543. In this regard, log table Rom 543 also has programmed therein 16 values of $\log_2(A + 1/16)$. The 6th through 9th bits of the number A are stored, as previously described, in shift register 542 and are conducted to magnitude comparator 554 via leads 542A. The magnitude comparator 544 is also supplied with a four bit number by number generator 545 via leads 545A. Number generator 545 may comprise a counter which is continuously stepped by a clock source, not illustrated, to provide a series of binary numbers on line 545A representing the 16 values assigned to $\log_2(A + 1/16)$ in log table Rom 543. Magnitude comparator 544 functions to provide a logic 0 output on output lead 544A when the number on lead 542A is equal to or less than the number on lead 545A, and which is a logic 1 when the number on lead 542A is greater than the number on lead 545A.

Log table Rom 543 is controlled by the signal on line 544A in the following manner. Whenever the signal on lead 544A is a logic 0, log table Rom 543 is enabled to provide an output signal on line 540A which represents $\log_2(A)$ comprising one of the values programmed therein of $\log_2(A)$. Whenever the signal on output lead 544A is a logic 1, however, log table Rom 543 is enabled to provide an output signal on line 540A which represents $\log_2(A + 1/16)$. comprising one of the values programmed therein of $\log_2(A + 1/16)$. Accordingly, the output signal on line 540A switches from $\log_2(A)$ to $\log_2(A + 1/16)$ at some point in the cycle established by number generator 545, which point is dependent upon the value of the least significant bits stored in shift register 542. This abrupt shift in value is averaged by D-to-A converter 550 which has a long time constant with respect to the cycle of number generator 545.

The read clock 602 continues to step the bit address generator 603 which produces, after twenty read clock cycles, an output pulse on line 603B. At this time, read cycle control 605 provides an output signal on line $600E_2$ which instructs sample and hold address decoder 612 to enable the sample and hold circuit 560 for a predetermined period of time. A signal is also supplied on line 605B for this predetermined period to inhibit the read clock 605. Previously, D/A converter 550 has changed the digital $\log_2$ value from the signals on lines 540A, 520B into a corresponding analog value and has supplied to the analog value sample and hold circuit 560 via lines 550A and $550A_2$. Accordingly the value $\log_2(TS_{cal} - TS_{clean\ air})$ for the wavelength $\lambda_1$ is stored in sample and hold circuit 560.

At the termination of the enable signal on line $600E_2$, read cycle control 605 removes the inhibit from the read clock 602 and initiates the sequence of fourth, fifth and sixth read intervals, repeating the sequence of CONTROL 1 and CONTROL 2 signals, as illustrated in more detail in FIG. 13. The operations of the measurement electronics can be understood by considering FIG. 13 in connection with FIG. 10.

At the conclusion of the sixth read interval, $\log_2(TS_{ambient}\ TS_{clean\ air})$ appears at the output 550A of D/A converter 550. During the sixth read interval, the read cycle control 605 provides an address signal on line $600E_3$ to sample and hold address decoder 612 which instructs sample and hold address decoder to address a circuit within sample and hold circuits 580 via line $600E_4$. Previously, difference amplifier 510 has accomplished the subtraction of $\log_2(TS_{cal} - TS_{clean\ air})$, which is stored in sample and hold circuit 560, from $\log_2(TS_{ambient} - TS_{clean\ air})$, which appears on the output 550A, and has added thereto the analog scaling constant $V_{sc}$. The result appears on line 570A and is stored in the addressed sample and hold circuit 580 when read cycle control 605 provides an enable signal on line $600E_2$.

This sequence is repeated during the seventh, eighth, an ninth read intervals illustrated in FIG. 13, in which the back scatter calculations are made.

The sequence of calculations just described is repeated for the $\lambda_2$ and $\lambda_3$ word groups in the tenth to twenty-seventh read intervals, not illustrated.

At the conclusion of the twenty-seventh read interval, read cycle control 605 rests accumulate-read register 609 to its first state via a signal on line 605C, wherein multipliers 613 and 614 are rest to their normal state in a logic 0 signal on line 609A. When read cycle control 605 returns the signal on line 605A to a logic 0, the inhibit is removed from multivibrator 606 and the next accumulating cycle begins.

The timing of the calibration cycle is illustrated in FIG. 12. The calibration cycle timer 610 provides an output on line 610A a predetermined intervals, for example, every fifteen minutes. At the termination of the next read cycle, as signified by the resetting of accumulate-read register 609 and the return of the output signal on line 609A to a logic 0 state, calibration cycle control 611 provides a logic 1 ouput signal on line 600F to close valve 439 and to open valves 438, 440, and 441, thereby circulating clean air through the nephelometer 410. Simultaneously, a logic 1 output signal is provided on line $600E_1$ to sample and hold address decoder 612 to instruct sample and hold address decoder 612 to inhibit the sampling of the sample and hold circuits 560, 580.

During the next accumulate cycle and the next read cycle, clean air is circulated through the nephelometer 410 to purge all traces of ambient air.

Two control lines, labeled 611A in FIG. 10, are provided from calibration cycle control signal 611 to write word generator 604. The CAL 1 and CAL 2 signals appearing on the control lines 611A are seen in FIG. 12. When both CAL 1 and CAL 2 are a logic 0, write word address generator 604 is instructed to address only the words $TS_{ambient}$ and $BS_{ambient}$ for wavelengths $\lambda_1$, $\lambda_2$, and $\lambda_3$ within memory 510. When the CAL 1 signal becomes a logic 1, which occurs at the same time that the signals on line 600F and $600E_1$ become a logic 1, the write word address generator 604 is instructed to address those word locations in memory 510 in which the clean air counts are to be stored. Throughout the succeeding accumulating cycle, the clean air counts for $\lambda_1$, $\lambda_2$, and $\lambda_3$ are accumulated. However, these counts are not utilized on the succeeding read cycle inasmuch as the sample and hold circuits 580 are inhibited by virtue of the logic 1 signal on line $600E_1$. During the succeeding erase cycle, these counts are erased from memory 510.

At the termination of the succeeding read cycle, calibration cycle control 611 changes the signal on line $600E_1$ to a logic $O$ state. In the next accumulating cycle, counts are accumulated and stored in memory 510 for the words $TS_{clean\ air}$ and $BS_{clean\ air}$ for the three wavelengths $\lambda_1$, $\lambda_2$, and $\lambda_3$ under control of write word address generator 604 and bit address generator 603. During the succeeding read cycle, the counts for the words $TS_{ambient}$ and $BS_{ambient}$ for $\lambda_1$, $\lambda_2$, and $\lambda_3$ that were obtained during the accumulating cycle immediately preceding the calibration cycle are used, along with the calibration counts obtained during the previous calibration cycle, and the clean air counts acquired during the present calibration cycle, to calculate new values of $b_{scat}$ and $b_{scat}$, as previously described.

At the termination of this read cycle, the CAL 1 signal returns to a logic 0 and the CAL 2 signal goes to a logic 1, thereby instructing the write word address generator 604 to address the words $TS_{cal}$ for $\lambda_1$, $\lambda_2$, and $\lambda_3$ in memory 510. Simultaneously, a logic 1 output signal is provided on a line 600G to cause the calibration scatterer 467 to be moved into the cone of observation. During the next accumulating cycle, counts are accumulated and stored in memory 510 for the word $TS_{cal}$ for the wavelengths $\lambda_1$, $\lambda_2$, and $\lambda_3$. (Counts obtained during the back scatter accumulating intervals are accumulated but not stored.) During the next read cycle, the new calibration counts are used to calculate new values of $b_{scat}$ and $b_{scat}$ in the manner previously described.

At the termination of this read cycle, the CAL 2 signal on line 611A is returned to a logic 0 and the signal on line $600E_1$ goes again to a logic 1. Similarly, the signals on line 600G and 600F return to a logic 0 state, thereby moving the calibration scatterer 467 out of the cone of observation and closing the valves 448 and 441 and opening valve 439, respectively. During the succeeding accumulate cycle and read cycle, the nephelometer 410 is filled with ambient air, but calculation of $b_{scat}$ and $b_{scat}$ is inhibited by the logic 1 signal on line $600E_1$.

At the termination of the read cycle, calibration cycle control 611 is reset by the signal on line 609A from accumulate-read register 607 and accordingly changes the signal on line $600E_1$ to a logic 0, thereby terminating the calibration cycle.

What is claimed is:

1. An integrating nephelometer for monitoring the visual qualities of an aerosol by determining the extinction coefficient due to light scattering thereof, comprising:
   a. a housing which includes a chamber, an inlet means for introducing the aerosol into said chamber and an outlet means for removing the aerosol from said chamber,
   b. means within housing which defines a cone of observation of said aerosol in said chamber, said cone of observation having an axis,
   c. a light source producing a continuous light output having a cosine emission characteristic,
   d. means positioning said light source so that said light sorce output illuminates said cone of observation and so that the maximum of the cosine emission characteristic lies at right angles to the axis of said cone of observation,
   e. a highly-sensitive, measurement photoelectric detector, and means positioning said measurement photoelectric detector with respect to said housing so that the portions of said light source output which are scattered by said aerosol and which pass through the vertex of said cone of observation are incident upon said measurement photoelectric detector, whereby said measurement photoelectric detector produces an output signal including a pulse for each photoelectron resulting from a detected photon and also including noise,
   f. a photon-detecting apparatus including means for removing said noise from said output signal and for providing an output pulse for each of said photoelectrons resulting in a pulse in said output signal whose amplitude exceeds the expected level of said noise, and
   g. measurement means coupled to said photon-detecting apparatus for converting the rate of occurrence of such output pulses into an output signal related in value to the desired extinction coefficient.

2. An integrating nephelometer as recited in claim 1, wherein said light source comprises a tungsten filament incandescent bulb, and an opal glass diffuser.

3. An integrating nephelometer as recited in claim 2, further comprising means regulating the intensity of said light source output at a constant value.

4. An integrating nephelometer as recited in claim 3, wherein said regulating means comprises a second photoelectric detector receiving light directly from said light source and providing an output signal proportional to the intensity thereof, and a lamp control and supply means for applying a regulated voltage across said tungsten filament incandescent bulb in response to said output signal.

5. An integrating nephelometer as recited in claim 1, wherein said highly sensitive measurement photoelectric detector comprises a multiplier phototube.

6. An integrating nephelometer as recited in claim 5, wherein said photon-detecting apparatus comprises means having said output signal from said measurement photoelectric detector applied thereto and operative to increase the duration of each of said pulses therein to provide a second signal, a source of a threshold signal, the magnitude of said threshold signal being set at a value which exceeds the expected level of said noise, and a level detector having said second signal and said threshold signal applied thereto and operative to provide said output pulse whenever the magnitude of said second signal exceeds that of said threshold signal.

7. An integrating nephelometer as recited in claim 6, wherein said photon-detecting apparatus further comprises an amplification means for amplifying said second signal before application thereof to said level detector.

8. An integrating nephelometer as recited in claim 6, wherein such of said pulses in said output signal from said measurement photoelectric detector includes an initial portion havng a short rise time and a terminal portion having a relatively long fall time, and further comprising means compressing said fall time portion before application of said second signal to said level detector.

9. An apparatus as recited in claim 5, further including means providing a compensation signal related in magnitude to the rate of thermally emitted electrons in said multiplier phototube, and means subtracting said compensation signal from said output signal from said measurement means.

10. An apparatus as recited in claim 9, further comprising a digital scale counter having an input and an output, said input having applied thereto said output pulses from said photon-detecting apparatus and said output being connected to said measurement means, said digital scale counter being operative to provide a pulse at its output for a predetermined number of pulses applied to said input, and scale control means connected to said digital scale counter and to said means providing a compensation signal for selecting said predetermined number in said digital scale counter and for varying said compensation signal for changes in said predetermined number.

11. An integrating nephelometer as recited in claim 1, further comprising a digital scale counter having an input and an output, said input having applied thereto said output pulses from said photon-detecting apparatus and said output being connected to said measurement means, said digital scale counter being operative to provide a pulse at its output for a predetermined number of pulses applied to said input, and scale control means connected to said digital scale counter for selecting said predetermined number.

12. An integrating nephelometer as recited in claim 9, further including means inhibiting said light source output to permit calibration of said means providing a compensation signal.

13. An integrating nephelometer as recited in claim 9, further comprising means correcting for variations in said light source output, said correcting means including a second photoelectric detector receiving light directly from said light source and providing an output signal having a magnitude proportional to the intensity thereof, a source of a pulsed output signal, time ratio control means varying the duty cycle of said pulsed output signal in proportion to the reciprocal of the magnitude of said output signal from said second photoelectric detector to provide a series of control pulses, and switch means responsive to said control pulses for connecting the output signal from said photoelectric detector to said photon-detecting apparatus, and for connecting said compensation to said subtracting means only for the duration of each of said control pulses.

14. An integrating nephelometer as recited in claim 5, wherein said measurement means includes a reversible counter means having an input terminal coupled to the output of said photon-detecting apparatus, an output terminal, and a control terminal, said reversible counter means being operative to accumulate said output pulses from said photon-detecting apparatus in a first direction whenever a first control signal is present at said control terminal and to accumulate said output pulses from said photon-detecting apparatus in a second, opposite direction whenever a second control signal is present at said control terminal, and to transfer the accumulated count in said counter means to said output terminal at the termination of said second control signal, a digital-to-analog signal conversion apparatus for converting the digital count appearing at the output terminal of said reversible counter means into a corresponding analog signal comprising an output signal proportional to the desired extinction coefficient, means operative to inhibit said light source output in response to a control signal, and control logic means operative to apply said control signal to said light source inhibiting means and said first control signal to said reversible counter means for a first, predetermined period of time, whereby said reversible counter means has located therein at the end of said first period a digital count proportional to said thermally emitted electrons, and further operative to remove said control signal from said light source inhibiting means and to apply said control signal to said reversible counter means for a second, predetermined period to time having a duration equal to that of said first period, whereby said reversible counter means has located therein at the end of said second period of time a count proportional only to said photoelectrons.

15. An integrating nephelometer as recited in claim 14, wherein said reversible counter means includes a first counter counting said output pulses signal, said first direction in response to said first control lsignal, a second counter, a transfer circuit responsive to the termination of said first control signal for transferring the accumulated count in said first counter into said second counter, said second counter being operative to count in said second direction from said accumulated count in response to said second control signal and further operative to transfer an accumulated count present therein at the termination of said second control signal to said digital-to-analog signal conversion means.

16. An integrating nephelometer as recited in claim 14, wherein said light source inhibiting means comprises an opaque shutter selectively interposed in the light path between said light source and said measurement photoelectric detector in response to said control signal.

17. An integrating nephelometer as recited in claim 14, for the measurement of the extinction coefficient due to light scattering at a plurality of wavelengths, wherein said light source inhibiting means includes a rotatable filter wheel movably mounted between said light source and said multiplier phototube, said rotatable filter wheel having an opaque portion of a plurality of filter portions, each of said plurality of filter portions screening all light but that of a distinct band of wavelengths, and further comprising a plurality of signal storage means, each of said signal storage means having an input terminal coupled to the output of said digital-to-analog signal conversion means and being responsive to sample said output upon the application of a control signal thereto, and wherein said control logic means further includes drive means operative to rotate said filter wheel so that said opaque portion and said plurality of filter portions are successively interposed between said light source and said measurement photoelectric detector, and means responsive to said drive means to apply said first and second control signals to said reversible counter and said control signals to said plurality of signal storage means, whereby said reversible counter means counts in said first direction whenever said opaque portion is interposed in said light path so that said reversible counter means counts in said first direction whenever said opaque portion is interposed in said light path so that said reversible counter means has located therein at the end of said first period an accumulated count proportional to said thermally emitted electrons, and whereby said reversible counter means counts in second or opposite directions for a plurality of successive periods of time, each identical in duration to that of said first period, when said plurality of said filter portions are successively interposed in said light path, and said plurality of signal storage means are successively operative at the end of each of said successive time periods to sample the accumulated count at the output terminal of said reversible counter means.

18. An integrating nephelometer as recited in claim 1, which additionally compensates said output signal representing the desired extinction coefficient for components thereof due to Rayleigh scatter and unwanted light reflections from surfaces in said chamber, further comprising:
  a. a source of particle-free air,
  b. valve means interposed in said inlet means for selectively circulating either the aerosol, or air from said source of particle-free air through said chamber in response to a control signal, and
  c. wherein said measurement means includes a reversible counter means having an input terminal coupled to the output of said photon-detecting apparatus, an output terminal, and a control terminal, said reversible counter means being operative to accumulate a count of said output pulses at its input terminal in a first direction whenever a first control signal is present at said control terminal, and to accumulate a count of the output pulses at its input terminal in a second, opposite direction, whenever a second control signal is present at said control signal, and a transfer of the accumulated count therein to said output terminal at the termination of said second control signal, a digital-to-analog signal conversion apparatus for converting the digital count appearing at the output terminal of said reversible counter means into a corresponding analog signal comprising an output signal representing the desired extinction coefficient, and control logic means operative to apply a first control signal to said valve means to cause said source to be coupled to said chamber, and to concurrently apply said first control signal to said reversible counter means for a first, predetermined period of time, whereby said reversible counter means has located therein at the end of said first period of count including components resulting only from Rayleigh scatter and unwanted light reflections, and wherein said control logic means is further operative to apply a second control signal to said valve means to cause the aerosol to be coupled to said chamber and to concurrently apply said second control signal for a second, predetermined period to time, having a duration equal to that of said first period, to said reversible counter means, whereby said reversible counter means has located therein at the end of said second period to time a count including a component resulting only from light scattering by particles in the aerosol.

19. An integrating nephelometer as recited in claim 1, for providing measurement of the extinction coefficient due to light scattering at a plurality of wavelengths, and further comprising:
  a. a plurality of said measurement photoelectric detectors, one such measurement photoelectric detector being provided for each of said plurality of wavelengths,
  b. beam-splitting means positioned in said housing so as to direct portions of said light source output which are scattered by said aerosol and which pass through the vertex of the cone of observation onto each of said plurality of measurement photoelectric detectors, said beam-splitting means further including a plurality of filter means, one such filter means being associated with one of said measurement photoelectric detectors and operative to screen from said one measurement photoelectric detector all portions of said light source output but those within a narrow band of wavelengths centering about a wavelength associated with said one measurement photoelectric detector, and
  c. a plurality of photon-detecting apparatus, each photon-detecting apparatus providing output pulses from the output signal of one of said plurality of measurement photoelectric detectors, and wherein said measurement means includes means for connecting the rate of occurrence of said output pulses from said plurality of photon-detecting apparatus into a corresponding plurality of output signals corresponding to the desired extinction coefficient at said plurality of wavelengths.

20. An integrating nephelometer as recited in claim 19, further comprising means compensating each of said measurement photoelectrical detector output signals for variations in intensity of said light source output.

21. An integrating nephelometer as recited in claim 20, wherein said compensation means includes second and third photoelectric detectors receiving light from said light source, and providing output signals proportional to the intensity thereof, first and second filter means interposed between said light source and said second and third photoelectric detectors, respectively and respectively operable to pass two separate and distinct bands of wavelengths, interpolation means coupled to said second and third photoelectric detectors and providing therefrom by approximation to Planck's equation a plurality of compensation signals, each compensation signal representing the intensity of said light source output at one of said wavelengths associated with one of said plurality of measurement photoelectric detectors, and means varying the output signal from each one of said plurality of measurement photoelectric detectors in response to the corresponding one of said plurality of compensation signals.

22. An integrating nephelometer as recited in claim 1, wherein said measurement means comprises means averaging the rate of occurrence of said output pulses over a predetermined time period to obtain an output signal which is porportional to the desired extinction coefficient.

23. An integrating nephelometer as recited in claim 22, wherein said averaging means comprises an averaging amplifier having an adjustable time constant, and control means for adjusting said time constant to vary said predetermined time period.

24. An integrating nephelometer as recited in claim 1, wherein said measurement means includes:
1. means accumulating said output pulses over a predetermined period of time to obtain a measurement count equal to the number of output pulses occuring during said predetermined period of time,
2. first means storing a clean air count equal to the number of output pulses that would occur during said predetermined period of time if said chamber were to be filled with clean, particle-free air, and
3. means subtracting said clean air count from said measurement count to obtain a compensated measurement count related in value to the component of the desired extinction coefficient resulting only from light scattering by particles in the aerosol.

25. An integrating nephelometer as recited in claim 24, wherein said measurement means further comprises a digital-to-analog conversion means coupled to said subtracting means for converting said compensated measurement count into an output signal proportional to the desired extinction coefficient.

26. An integrating nephelometer as recited in claim 24, further comprising second means storing a compensated calibration count related in value to the component of the extinction coefficient resulting only from light scattering by particles in an aerosol of known composition, and means dividing said compensated measurement count by said compensated calibration count to obtain a normalized measurement count which is compensated for long-term drift in said photoelectric detector and in said light source.

27. An integrating nephelometer as recited in claim 26, further comprising third means storing a calibration count equal to the number of output pulses that would occur during said predetermined period of time if said chamber were to be filled with such aerosol of known composition, and second means subtracting said clean air count from said calibration count to obtain said compensated calibration count.

28. An integrating nephelometer as recited in claim 26, wherein said measurement means further comprises a digital-to-analog conversion means coupled to said dividing means for converting said normalized measurement count into an output signal proportional to the desired extinction coefficient.

29. An integrating nephelometer as recited in claim 26, wherein said dividing means comprises means separating said compensated measurement count and said compensated calibration count each into first and second numbers, each such first number comprising a quantity $n$ and each such second number comprising a quantity $A$ in a relation $2^n(A)$, $1 \le A<2$; means operative on each of such second numbers to obtain third numbers therefrom each equal to $\log_2(A)$, means obtaining the sums of such first and such third numbers for said compensated measurement count and for said compensated calibration count, and means subtracting the resulting sum for said compensated calibration count from the resultant sum for said compensated measurement count to obtain said normalized measurement count.

30. An integrating nephelometer as recited in claim 24, further comprising a source of particle-free air, means for circulating air from said source of particle-free air through said chamber, second means accumulating said output pulses from said photon-detecting apparatus over a period of time equal in duration to said predetermined period of time to obtain said clean air count, and means transferring said clean air count to said first storing means.

31. An integrating nephelometer as recited in claim 30, further comprising a calibration scatterer, which is designed to produce light scatter in said chamber corresponding to that which would be obtained if such chamber were to be filled with an aerosol of known composition, means interposing said calibration scatterer in said cone of observation, third means accumulating said output pulses from said photon-detecting apparatus over a period of time equal in duration to that of said predetermined period of time when said chamber is filled with air from said source of particle-free air and said calibration scatterer is interposed in said cone of observation to obtain a calibration count equal to the number of output pulses occurring during said period of time, second means subtracting said clean air count from said calibration count to obtain a compensated calibration count related in value to the component of the extinction coefficient resulting only from light scattered by particles in said aerosol, and means dividing said compensated measurement count by said compensated calibration count to obtain a normalized measurement count which is compensated for long-term drift in said photoelectric detector and in said light source.

32. An integrating nephelometer as recited in claim 30, wherein said calibration scatterer comprises an object whose reflectance does not vary with wavelength.

33. An integrating nephelometer as recited in claim 24, further comprising back scatter means blocking light from said light source over scattering angles substantially in the range of 0° to 90° from reaching said cone of observation, whereby said compensated measurement count is related in value only to the back scatter component of the desired extinction coefficient.

34. An integrating nephelometer as recited in claim 1, further comprisng back scatter means blocking light from said light source over scattering angles substantially in the range of 0° to 90° from reaching said cone of observation, whereby said output signal from said measurement means is related in value only to the back scatter component of the desired extinction coefficient.

35. An integrating nephelometer as recited in claim 1, wherein said measurement means includes:
1. timing and control logic means providing a plurality of control signals establishing a plurality of successive measurement cycles, said plurality of control signals also dividing each of said measurement cycles into an accumulating cycle and a read cycle, the duration of each accumulating cycle being equal to a predetermined period of time,
2. digital memory means including a plurality of storage locations grouped into a plurality of digital words including a measurement count word, a clean air count word, and a calibration count word, said clean air count word containing a clean air count equal to the number of output pulses from said photon-detecting apparatus that would occur during said predetermined period of time if said chamber were to be filled with clean, particle-free air, and said calibration count word containing a calibration count equal to the number of said output pulses that would occur during said predetermined period of time if said chamber were to be filled with an aerosol of known composition, 3. means accumulating said output pulses in said measurement count word under control of said control signals so that said measurement count word contains at the end of each said accumulating cycle a measurement count equal to the number of said output pulses occurring during said predetermined period of time, 4. calculation means operable during each said read cycle under control of said control signals to subtract said clean air count from said calibration count to obtain a compensated calibration count, to subtract said clean air count from said measurement count obtained during the preceding accumulating cycle to obtain a compensated measurement count, and to divide said compensated measurement count by said compensated calibration count to obtain a normalized measurement count which is related in value to the component of a desired extinction coefficient resulting only from light scattering by particles in the aerosol and which is compensated for long-term drift in said photoelectric detector and in said light source.

36. An integrating nephelometer as recited in claim 35, wherein said measurement means further includes a digital-to-analog conversion means coupled to said calculation means for converting said normalized measurement count in each read cycle into a corresponding analog signal proportional to the desired extinction coefficient.

37. An integrating nephelometer as recited in claim 36, wherein said measurement means comprises an analog storage means operable under control of said control signals to sample said analog signal during each read cycle and to store the value of the analog signal so sampled until the succeeding read cycle.

38. An integrating nephelometer as recited in claim 35,
   a. further comprising back scatter means for selectively blocking light from said light source over scattering angles substantially in the range of 0° to 90° from reaching said cone of observation, and
   b. wherein
      1. said plurality of control signals from said timing and control logic means also divide each said accumulating cycle into a plurality of accumulating intervals, said plurality of accumulating intervals being further divided into first and second groups, each of said first and second groups including at least one accumulating interval and each having a total duration in an accumulating cycle which is substantially equal to said predetermined period of time,
      2. said plurality of digital words in said digital memory further include a back scatter measurement count word and a back scatter clean air count word, said back scatter clean air count word storing a back scatter clean air count equal to the number of output pulses from said photon-detecting apparatus that would occur during said predetermied period of time if said chamber were to be filled with clean, particle-free air and if light from said light source over scattering angles substantially in the range of 0° to 90° were blocked from reaching said cone of observation,
      3. said back scatter means is operable under control of said control signals only during said first group of accumulating intervals in each said accumulating cycle,
      4. said accumulating means is operable under control of said control signals to accumulate said output pulses in said back scatter measurement count word for said first group of accumulating intervals so that said back scatter measurement count word contains at the end of each said accumulating cycle a back scatter measurement count equal to the number of said output pulses occurring during said predetermined period of time when light from said light source reaches said cone of observation over scattering angles not blocked by said back scatter means, and said accumulating means is operable under control of said control signals to accumulate said output pulses in said measurement count word for said second group of accumulating intervals so that said measurement count word contains at the end of each said accumulating cycle a measurement count equal to the number of said output pulses occurring during said predetermined period of time when light from said light source reaches said cone of observation over substantially all scattering angles,
      5. said calculation means is further operable during each said read cycle under control of said control signals to subtract said back scatter clean air count from said back scatter measurement count obtained during the preceding accumulating cycle to obtain a compensated back scatter measurement count, and to divide said compensated back scatter measurement count by said compensated calibration count to obtain a normalized back scatter measurement count which is related in value to the back scatter component of the desired extinction coefficient resulting only from light scattering by particles in the aerosol and which is compensated for long-term drift in said photoelectric detector and in said light source.

39. An integrating nephelometer as recited in claim 38, wherein said measurement means further includes a digital-to-analog conversion means coupled to said calculation means for converting said normalized measurement count and said normalized back scatter measurement count in each read cycle into first and second corresponding analog signals respectively proportional to the desired extinction coefficient and to the back scatter component thereof.

40. An integrating nephelometer as recited in claim 39, wherein said measurement means further comprising an analog storage means operable under control of said control signals to sample said first and second analog signals during each read cycle and to store the values of the first and second analog signals so sampled until the succeeding read cycle.

41. An integrating nephelometer as recited in claim 38, wherein said plurality of control signals from said timing and control logic means define an accumulating cycle in which the accumulating intervals in said first and second groups alternate in time.

42. An integrating nephelometer as recited in claim 38, wherein said back scatter means comprises drive means including an output mechanism which is placed in first or second positions in response to said control signals from said timing and control logic means, and shutter means attached to and movable with said output mechanism for blocking light from said light source only when said output mechanism is in said first position.

43. An integrating nephelometer as recited in claim 35,
   a. further comprising
      1. a source of particle-free air,
      2. first means selectively circulating air from said source or particle-free air through said chamber,
      3. a calibration scatterer, said calibration scatterer designed to produce light scatter in said chamber corresponding to that which would be obtained if said chamber were to be filled with an aerosol of known composition,
      4. second means selectively interposing said calibration scatterer in said cone of observation, and
   b. wherein
      1. said plurality of control signals from said timing and control logic means establish first and second calibration accumulating cycles, theh duration of each of said first and second calibration accumulating cycles being equal to said predetermined period of time,
      2. said first means is operable under control of said control signals during said first and second calibraton accumulating cycles,
      3. said accumulating means is operable under control of said control signals to accumulate said output pulses in said clean air word during said first calibraton accumulating cycle so that clean air word contains at the end of said first calibration accumulating cycle said clean air count,
      4. said second means is operable under control of said control signals only during said second calibration cycle, and
      5. said accumulating means is operable under control of said control signals to accumulate said output pulses in said calibration word during said second calibration accumulating cycle so that said calibration word contains at the end of said second calibration accumulating cycle said calibration count.

44. An integrating nephelometer as recited in claim 43, wherein said first and said second calibration accumulating cycles are repeated periodically.

45. An integrating nephelometer as recited in claim 43, wherein said calibration scatterer comprises an object whose reflectance does not vary with wavelength.

46. An integrating nephelometer as recited in claim 45, wherein said second means comprises means including an output mechanism which is placed in first or second positions in response to said control signals from said timing and control logic means, said object being attached to and movable with said output mechanism and being interposed in said cone of observation only when said output mechanism is in said first position.

* * * * *

UNITED STATES PATENT AND TRADEMARK OFFICE
CERTIFICATE OF CORRECTION

PATENT NO. : 3,953,127
DATED : April 27, 1976
INVENTOR(S) : Norman C. Ahlquist et al It is certified that error appears in the above-identified patent and that said Letters Patent are hereby corrected as shown below:

Column 35, line 16 "havng" should be --having--

Column 36, line 40, delete "signal", and after the word "pulses" add --in--

Column 36, line 41, delete "1signal" and insert --signal--

Column 36, line 64, "of" should be --and--

Column 37, line 65 delete the second occurrence of "of" and insert therefor --a--

Signed and Sealed this

Twenty-sixth Day of October 1976

[SEAL]

Attest:

RUTH C. MASON
Attesting Officer

C. MARSHALL DANN
Commissioner of Patents and Trademarks